United States Patent
Marin y Kall et al.

(10) Patent No.: US 12,151,099 B2
(45) Date of Patent: *Nov. 26, 2024

(54) TRANSVENOUS INTRACARDIAC PACING CATHETER HAVING IMPROVED LEADS

(71) Applicant: SWIFT SYNC, INC., Miami Shores, FL (US)

(72) Inventors: Christian Marin y Kall, Miami Shores, FL (US); Eduardo De Marchena, Miami, FL (US); Mark Carlson, Barrington, IL (US); Sai Nimmagadda, Barrington, IL (US)

(73) Assignee: SWIFT SYNC, INC., Miami Shores, FL (US)

( * ) Notice: Subject to any disclaimer, the term of this patent is extended or adjusted under 35 U.S.C. 154(b) by 9 days.

This patent is subject to a terminal disclaimer.

(21) Appl. No.: 18/358,961

(22) Filed: Jul. 26, 2023

(65) Prior Publication Data

US 2023/0364418 A1  Nov. 16, 2023

Related U.S. Application Data

(63) Continuation-in-part of application No. 17/453,490, filed on Nov. 4, 2021, and a continuation-in-part of application No. 17/478,979, filed on Sep. 20, 2021, now Pat. No. 11,638,818, and a continuation of application No. 17/463,327, filed on Aug. 31, 2021, (Continued)

(51) Int. Cl.
*A61N 1/05* (2006.01)
*A61M 25/00* (2006.01)
*A61M 25/09* (2006.01)

(52) U.S. Cl.
CPC .......... *A61N 1/056* (2013.01); *A61M 25/0026* (2013.01); *A61M 25/09* (2013.01); *A61M 2205/0266* (2013.01)

(58) Field of Classification Search
CPC .............. A61N 1/3622; A61N 1/36843; A61N 1/36139
See application file for complete search history.

(56) References Cited

U.S. PATENT DOCUMENTS

| 4,146,036 A | 3/1979 | Dutcher et al. |
| 4,471,777 A | 9/1984 | McCorkle, Jr. |

(Continued)

OTHER PUBLICATIONS

TCT Conference Powerpoint 2019, Sep. 25, 2019-Sep. 29, 2020, Christian Marin y Kall, Eduardo DeMarchena, Transcatheter Cardiovascular Therapeutics (TCT) Conference in San Francisco, Swift Sync Temporary Synchronic.

(Continued)

*Primary Examiner* — Alyssa M Alter
(74) *Attorney, Agent, or Firm* — JUNEAU & MITCHELL; Todd L. Juneau

(57) ABSTRACT

The embodiments described herein relate to a self-positioning, quick-deployment low profile transvenous electrode system for sequentially pacing both the atrium and ventricle of the heart in the "dual chamber" mode having an atraumatic tip comprising a domed head connected to a cylindrical sidewall, said cylindrical sidewall having a sloped proximal edge connected to a tapered coupling, said tapered coupling forming a smooth transition to an outer diameter of the insulated wire, and methods for deploying the same.

40 Claims, 26 Drawing Sheets

Related U.S. Application Data and a continuation of application No. 17/206,359, filed on Mar. 19, 2021, and a continuation of application No. PCT/IB2021/052251, filed on Mar. 18, 2021, and a continuation of application No. 17/153,875, filed on Jan. 20, 2021, now abandoned.

(56) References Cited

U.S. PATENT DOCUMENTS

| | | |
|---|---|---|
| 4,576,162 A | 3/1986 | McCorkle |
| 4,582,056 A | 4/1986 | McCorkle, Jr. |
| 4,884,567 A | 12/1989 | Elliott et al. |
| 4,946,457 A | 8/1990 | Elliott |
| 5,353,800 A | 10/1994 | Pohndorf et al. |
| 5,575,766 A | 11/1996 | Swartz et al. |
| 5,639,276 A | 6/1997 | Weinstock et al. |
| 5,674,217 A | 10/1997 | Wahlstrom et al. |
| 5,727,552 A | 3/1998 | Ryan |
| 5,871,532 A | 2/1999 | Schroeppel |
| 5,957,966 A | 9/1999 | Schroeppel et al. |
| 6,038,472 A | 3/2000 | Williams et al. |
| 6,125,290 A | 9/2000 | Miesel |
| 6,125,291 A | 9/2000 | Miesel et al. |
| H1905 H | 10/2000 | Hill |
| 6,134,459 A | 10/2000 | Roberts et al. |
| 6,144,866 A | 11/2000 | Miesel et al. |
| 6,198,952 B1 | 3/2001 | Miesel |
| 6,228,052 B1 | 5/2001 | Pohndorf |
| 6,295,476 B1 | 9/2001 | Schaenzer |
| 6,419,674 B1 | 7/2002 | Bowser et al. |
| 6,564,096 B2 | 5/2003 | Mest |
| 6,714,823 B1 | 3/2004 | De Lurgio et al. |
| 6,738,655 B1 | 5/2004 | Sen et al. |
| 6,766,200 B2 | 7/2004 | Cox |
| 7,004,176 B2 | 2/2006 | Lau |
| 7,274,966 B2 | 9/2007 | Sommer et al. |
| 7,311,731 B2 | 12/2007 | Lesniak et al. |
| 7,519,424 B2 | 4/2009 | Dennis et al. |
| 7,547,301 B2 | 6/2009 | Altman et al. |
| 7,616,992 B2 | 11/2009 | Dennis et al. |
| 7,630,761 B2 | 12/2009 | Salo et al. |
| 7,658,727 B1 | 2/2010 | Fernandes et al. |
| 7,935,075 B2 | 5/2011 | Tockman et al. |
| 7,949,411 B1 | 5/2011 | Yang et al. |
| 7,976,551 B1 | 7/2011 | Gutfinger et al. |
| 8,012,127 B2 | 9/2011 | Lieberman et al. |
| 8,012,143 B1 | 9/2011 | Kampa et al. |
| 8,036,757 B2 | 10/2011 | Worley |
| 8,142,363 B1 | 3/2012 | Eigler et al. |
| 8,150,535 B2 | 4/2012 | Tockman et al. |
| 8,211,084 B2 | 7/2012 | Kassab et al. |
| 8,260,435 B2 | 9/2012 | Johnson et al. |
| 8,321,013 B2 | 11/2012 | Darvish et al. |
| 8,328,752 B2 | 12/2012 | Kassab et al. |
| 8,346,372 B2 | 1/2013 | Yang et al. |
| 8,364,281 B2 | 1/2013 | Duncan et al. |
| 8,403,866 B2 | 3/2013 | Seifert et al. |
| 8,442,656 B2 | 5/2013 | Tockman et al. |
| 8,480,662 B2 | 7/2013 | Stolen et al. |
| 8,509,916 B2 | 8/2013 | Byrd et al. |
| 8,676,349 B2 | 3/2014 | Stalker et al. |
| 8,712,544 B2 | 4/2014 | Dabney et al. |
| 8,751,018 B1 | 6/2014 | Sethna et al. |
| 8,758,372 B2 | 6/2014 | Cartledge et al. |
| 8,938,310 B2 | 1/2015 | Spotnitz et al. |
| 8,945,145 B2 | 2/2015 | Tran et al. |
| 9,031,647 B2 | 5/2015 | Maskara et al. |
| 9,031,670 B2 | 5/2015 | Dabney et al. |
| 9,050,064 B2 | 6/2015 | Kassab et al. |
| 9,168,380 B1 | 10/2015 | Greenhut et al. |
| 9,242,098 B2 | 1/2016 | Madjarov et al. |
| 9,265,938 B2 | 2/2016 | Gaudiani |
| 9,446,232 B2 | 9/2016 | Duncan et al. |
| 9,526,891 B2 | 12/2016 | Eggen et al. |
| 9,597,514 B2 | 3/2017 | Khairkhahan et al. |
| 9,610,438 B2 | 4/2017 | Schilling |
| 9,656,063 B2 | 5/2017 | Kelley et al. |
| 9,737,264 B2 | 8/2017 | Braido et al. |
| 9,808,629 B2 | 11/2017 | Steingisser et al. |
| 9,889,312 B2 | 2/2018 | Bodner et al. |
| 9,955,999 B2 | 5/2018 | Kassab et al. |
| 9,999,774 B2 | 6/2018 | Cinbis et al. |
| 10,076,403 B1 | 9/2018 | Eigler et al. |
| 10,098,695 B2 | 10/2018 | Asirvatham et al. |
| 10,124,175 B2 | 11/2018 | Berthiaume et al. |
| 10,213,304 B2 | 2/2019 | Kapadia |
| 10,232,170 B2 | 3/2019 | Sparks et al. |
| 10,441,777 B2 | 10/2019 | Paspa et al. |
| 10,471,250 B2 | 11/2019 | Reddy |
| 10,537,731 B2 | 1/2020 | Reddy |
| 10,603,487 B2 | 3/2020 | Tockman et al. |
| 10,646,720 B2 | 5/2020 | Reddy |
| 10,667,910 B2 | 6/2020 | Bishop et al. |
| 10,780,280 B2 | 9/2020 | Friedman et al. |
| 10,786,679 B2 | 9/2020 | Reddy et al. |
| 10,806,932 B2 | 10/2020 | Koop et al. |
| 10,850,067 B2 | 12/2020 | Reddy et al. |
| 10,905,885 B2 | 2/2021 | Sanghera et al. |
| 10,925,706 B2 | 2/2021 | Eigler et al. |
| 10,980,570 B2 | 4/2021 | Reddy et al. |
| 11,020,075 B2 | 6/2021 | Liu et al. |
| 11,305,127 B2 | 4/2022 | Klepfer et al. |
| 11,383,080 B2 | 7/2022 | Tockman et al. |
| 11,420,046 B2 | 8/2022 | Daniels et al. |
| 11,534,602 B2 | 12/2022 | Reddy et al. |
| 11,577,075 B1 | 2/2023 | Gaudiani |
| 11,583,658 B2 | 2/2023 | Yang et al. |
| 11,638,818 B2 * | 5/2023 | Marin Y Kall ... A61M 25/0133 607/123 |
| 11,648,397 B1 | 5/2023 | Gaudiani |
| 11,684,475 B2 | 6/2023 | Bishop et al. |
| 11,690,978 B2 | 7/2023 | Schmidt et al. |
| 11,697,024 B2 | 7/2023 | Friedman et al. |
| 2002/0016622 A1 | 2/2002 | Janke et al. |
| 2002/0065544 A1 | 5/2002 | Smits |
| 2002/0072737 A1 | 6/2002 | Belden et al. |
| 2002/0077684 A1 | 6/2002 | Clemens et al. |
| 2002/0077685 A1 | 6/2002 | Sundquist et al. |
| 2002/0111663 A1 | 8/2002 | Dahl et al. |
| 2002/0128636 A1 | 9/2002 | Chin et al. |
| 2003/0083654 A1 | 5/2003 | Chin et al. |
| 2003/0092995 A1 | 5/2003 | Thompson |
| 2003/0163128 A1 | 8/2003 | Patil et al. |
| 2004/0002740 A1 | 1/2004 | Lee |
| 2004/0215139 A1 | 10/2004 | Cohen |
| 2004/0236395 A1 | 11/2004 | Iaizzo et al. |
| 2005/0010095 A1 | 1/2005 | Stewart et al. |
| 2005/0215991 A1 | 9/2005 | Altman |
| 2006/0036306 A1 | 2/2006 | Heist et al. |
| 2006/0064150 A1 | 3/2006 | Heist et al. |
| 2006/0247751 A1 | 11/2006 | Seifert |
| 2006/0253179 A1 | 11/2006 | Goode et al. |
| 2007/0083217 A1 | 4/2007 | Eversull et al. |
| 2007/0100439 A1 | 5/2007 | Cangialosi et al. |
| 2007/0208402 A1 | 9/2007 | Helland et al. |
| 2007/0255396 A1 | 11/2007 | Douk et al. |
| 2007/0282413 A1 | 12/2007 | Tockman et al. |
| 2008/0039904 A1 | 2/2008 | Bulkes et al. |
| 2008/0051840 A1 | 2/2008 | Moaddeb et al. |
| 2008/0071341 A1 | 3/2008 | Goode et al. |
| 2008/0109069 A1 | 5/2008 | Coleman et al. |
| 2008/0183267 A1 | 7/2008 | D'Aquanni et al. |
| 2008/0283066 A1 | 11/2008 | Delgado et al. |
| 2008/0312712 A1 | 12/2008 | Penner |
| 2008/0312725 A1 | 12/2008 | Penner |
| 2009/0005845 A1 | 1/2009 | David et al. |
| 2009/0053208 A1 | 2/2009 | Nayak |
| 2009/0264859 A1 | 10/2009 | Mas |
| 2009/0264863 A1 | 10/2009 | Bloom |
| 2010/0023088 A1 | 1/2010 | Stack et al. |
| 2010/0137936 A1 | 6/2010 | Dennis et al. |
| 2010/0185044 A1 | 7/2010 | Kassab et al. |
| 2010/0217367 A1 | 8/2010 | Belson |
| 2011/0022168 A1 | 1/2011 | Cartledge |

(56) References Cited

U.S. PATENT DOCUMENTS

| | | |
|---|---|---|
| 2011/0054582 A1 | 3/2011 | Dabney et al. |
| 2011/0144572 A1 | 6/2011 | Kassab et al. |
| 2011/0224720 A1 | 9/2011 | Kassab et al. |
| 2011/0238078 A1 | 9/2011 | Goode et al. |
| 2012/0016311 A1 | 1/2012 | Altman et al. |
| 2012/0059389 A1 | 3/2012 | Larson et al. |
| 2012/0130320 A1 | 5/2012 | Kassab et al. |
| 2012/0191181 A1 | 7/2012 | Kassab et al. |
| 2012/0290021 A1 | 11/2012 | Saurkar et al. |
| 2013/0131591 A1 | 5/2013 | Berthiaume et al. |
| 2014/0039612 A1 | 2/2014 | Dolan |
| 2015/0080977 A1 | 3/2015 | Stancer et al. |
| 2015/0094735 A1 | 4/2015 | Ward et al. |
| 2015/0207484 A1 | 7/2015 | Stevenson et al. |
| 2015/0231374 A1 | 8/2015 | Kassab et al. |
| 2015/0238729 A1 | 8/2015 | Jenson et al. |
| 2015/0320330 A1 | 11/2015 | Sparks et al. |
| 2015/0321011 A1 | 11/2015 | Carney et al. |
| 2016/0220811 A1 | 8/2016 | Spotnitz et al. |
| 2016/0250474 A1 | 9/2016 | Stack et al. |
| 2016/0302925 A1 | 10/2016 | Keogh et al. |
| 2017/0079780 A1 | 3/2017 | Schweich, Jr. et al. |
| 2017/0128719 A1 | 5/2017 | Boogaard |
| 2018/0028264 A1 | 2/2018 | Onik et al. |
| 2018/0036514 A1 | 2/2018 | Kassab et al. |
| 2018/0110561 A1 | 4/2018 | Levin et al. |
| 2018/0133463 A1 | 5/2018 | Reddy |
| 2018/0153615 A1 | 6/2018 | Madjarov et al. |
| 2018/0185153 A1 | 7/2018 | Bishop et al. |
| 2018/0256890 A1 | 9/2018 | Fuhs et al. |
| 2018/0296824 A1 | 10/2018 | De Kock et al. |
| 2019/0038906 A1 | 2/2019 | Koop et al. |
| 2019/0054289 A1 | 2/2019 | Reddy et al. |
| 2019/0083123 A1 | 3/2019 | Ollivier |
| 2019/0105490 A1 | 4/2019 | Daniels et al. |
| 2019/0142371 A1 | 5/2019 | Dykes et al. |
| 2019/0183576 A1 | 6/2019 | Fahim et al. |
| 2019/0269929 A1 | 9/2019 | Bjorklund et al. |
| 2019/0298989 A1 | 10/2019 | Gardeski et al. |
| 2019/0336779 A1 | 11/2019 | Nelson et al. |
| 2020/0101279 A1 | 4/2020 | Drake et al. |
| 2020/0138319 A1 | 5/2020 | Spector |
| 2020/0155798 A1 | 5/2020 | Yang et al. |
| 2020/0179045 A1 | 6/2020 | Levin et al. |
| 2020/0197706 A1 | 6/2020 | Grenz et al. |
| 2020/0330780 A1 | 10/2020 | Asirvatham et al. |
| 2020/0383717 A1 | 12/2020 | Lederman et al. |
| 2021/0001085 A1 | 1/2021 | Schmidt et al. |
| 2021/0060340 A1 | 3/2021 | Klepfer et al. |
| 2021/0077810 A1 | 3/2021 | Reddy |
| 2021/0137579 A1 | 5/2021 | Rafiee et al. |
| 2021/0138239 A1 | 5/2021 | Marin Y Kall et al. |
| 2021/0161637 A1 | 6/2021 | Eigler et al. |
| 2022/0054829 A1 | 2/2022 | Ward et al. |
| 2022/0193397 A1* | 6/2022 | Marin Y Kall ..... A61M 25/005 |
| 2022/0226642 A1* | 7/2022 | Marin Y Kall ......... A61L 29/18 |
| 2022/0257315 A1 | 8/2022 | Levin et al. |
| 2022/0338983 A1 | 10/2022 | Drasler |
| 2022/0409239 A1 | 12/2022 | Fischell et al. |
| 2022/0409357 A1 | 12/2022 | Eigler et al. |
| 2023/0001184 A1 | 1/2023 | Marin Y Kall et al. |
| 2023/0041152 A1 | 2/2023 | Gifford, III et al. |
| 2023/0285133 A1 | 9/2023 | Eigler et al. |

OTHER PUBLICATIONS

J. Cardiac Surgery, 2022:1-6, DOI 10:1111, JOCS 16796, Apr. 26, 2022, Perez, Ebner, Marin y Kall, Mitrani, de Marchena, Wiley Periodicals, A novel temporary atrioventricular sequential pacing catheter-Characteristics and first-in-human application.

* cited by examiner

DETAIL C
SCALE 2 : 3

FIG. 14 - dual lumen

FIG. 15 - multi-lumen

FIG. 18

| Sex distribution (n=10): | 9 men | 1 woman |
|---|---|---|
| Age (mean): | 60 ||

| Mean | | Range | |
|---|---|---|---|
| Height | 168cm | Height | 158-180cm |
| Weight | 77kg | Weight | 41-100kg |
| Baseline HR | 69bpm | Baseline HR | 55-80pbm |
| RV longitudinal dimension | 6.1cm | | |
| RA minor dimension | 4/1cm | | |
| RA area | 15.88cm² | | |

FIG. 19

| Subject | Lead | Impedance (ohms at V) | Threshold (V at ms) | Current (mA) |
|---|---|---|---|---|
| 001 | Atrial | 1,303 at 5.0 | 1.4 at 0.50 | 1.5 |
|  | RV | 684 at 5.0 | 3.0 at 0.50 | 5.4 |
| 002 | Atrial | 1,169 at 5.0 | 1.0 at 0.50 | 1.1 |
|  | RV | 735 at 5.0 | 1.0 at 0.50 | 0.7 |
| 003 | Atrial | 1,626 at 5.0 | 3.5 at 0.50 | 4.7 |
|  | RV | 775 at 5.0 | 1.1 at 0.50 | 0.8 |
| 004 | Atrial | 749 at 5.0 | 3.0 at 0.50 | 4.4 |
|  | RV | 1,078 at 5.0 | 0.3 at 0.50 | 0.2 |
| 005 | Atrial | 930 at 5.0 | 0.8 at 0.50 | 1 |
|  | RV | 1,249 at 5.0 | 0.5 at 0.50 | 0.4 |
| 006 | Atrial | 715 at 5.0 | 2.0 at 0.50 | 2.9 |
|  | RV | 618 at 5.0 | 0.9 at 0.50 | 1.4 |
| 007 | Atrial | <200 at 5.0 | 4.0 at 0.50 | >25.0 |
|  | RV | 709 at 5.0 | 4.0 at 0.50 | 7.8 |
| 008 | Atrial | 1,044 at 5.0 | 2.0 at 0.50 | 2.3 |
|  | RV | 677 at 5.0 | 1.0 at 0.50 | 1.1 |
| 009 | Atrial | 1,494 at 5.0 | 1.2 at 0.50 | 1.1 |
|  | RV | 2,510 at 5.0 | 1.5 at 0.50 | 1.1 |
| 010 | Atrial | 914 at 5.0 | 1.0 at 0.50 | 1.3 |
|  | RV | 1,022 at 5.0 | 2.0 at 0.50 | 2.1 |

Step 1:
Deploy the
transvenous intracardiac pacing catheter
to the right ventricle of a patient.

Step 2:
Partially withdraw the outer sheath to
a first position to expose
the inner ventricular sheath.

Step 3:
Partially withdraw the inner ventricular sheath to deploy the
shape-set ventricular pacing leads.

Step 4:
Calibrate the ventricle leads and withdraw and
re-deploy the ventricle leads from the inner ventricular sheath
as needed.

Step 5:
Partially withdraw the outer sheath to
a second position to expose
the inner atrial sheath.

Step 6:
Partially withdraw the inner atrial sheath to deploy the
shape-set atrial pacing leads.

Step 7:
Calibrate the atrial leads and withdraw and
re-deploy the atrial leads from the inner atrial sheath
as needed.

TRANSVENOUS INTRACARDIAC PACING CATHETER HAVING IMPROVED LEADS

FIELD OF THE INVENTION

The invention relates generally to medical devices that provide heart pacemaking function, and more particularly to a self-positioning, quick-deployment low profile transvenous electrode system for sequentially pacing both the atrium and ventricle of the heart in the "dual chamber" mode having an atraumatic tip comprising a domed head connected to a cylindrical sidewall, said cylindrical sidewall having a sloped proximal edge connected to a tapered coupling, said tapered coupling forming a smooth transition to an outer diameter of the insulated wire, and methods for deploying the same.

BACKGROUND

The heart requires to be paced temporarily during or after certain medical procedures or conditions like open heart surgery, heart attack, some infections, electrolyte disturbances, cardiac trauma or other issues. The only available temporary pacing catheters will not pace the heart in atrio-ventricular (AV) synchrony (only the right ventricle is paced).

Establishing and maintaining atrio-ventricular (AV) synchrony in a patient is important for achieving optimal cardiovascular hemodynamics. AV synchrony is estimated to increase stroke volume by as much as 50% in a normal heart and increase cardiac index by as much as 25% to 30%.

After open heart surgery, pacing is performed using epicardial wires that are lightly sutured to the epicardium before the thorax is closed. Once these epicardial wires are no longer needed, these pacing wires are pulled through the skin. Pulling the pacing wires represents a risk of a cardiac tamponade that can lead to death, and can also pose a risk of infection, myocardial damage, ventricular arrhythmias and perforation.

Existing temporary pacing catheters are also difficult to position correctly and often add complications including, in the case of balloon positioning, having the catheter move to and block the right ventricle outflow tract and the pulmonary artery.

Existing pacing catheter leads can also move (dislodge) either while pacing or at a critical point during a specific procedure like rapid pacing. For this reason, the mobility of the patient (ambulation) is limited when being temporary paced. Limited ambulation is known to increase the length of stay in certain scenarios and lead to higher healthcare costs.

Another problem concerns endothelial injury and fibrotic processes caused by pacing leads. Thrombotic obstruction can occur when leads introduce stasis or blood-flow problems, or if the leads contain a non-biocompatible, thrombogenic material. This can lead to neointimal fibrotic lead encapsulation within a short time. Another problem concerns contact-injury of leads with trabeculae carnae and other heart structures. Contact injury can include pressure-type inflammation or ulceration, as well as tissue damage from shear and friction forces. This damage can lead to more serious tissue damage or the scar tissue resulting from it can require the energy provided to the lead to be increased over time.

Accordingly, there is a need for an AV sequential pacing catheter that is easy to insert and position within the chambers of the heart, and which avoids endothelial injury to replace the current available temporary catheters/leads.

SUMMARY

The embodiments described herein are directed to an insertable atrio-ventricular sequential pacing catheter having an atraumatic tip comprising a domed head connected to a cylindrical sidewall, said cylindrical sidewall having a sloped proximal edge connected to a tapered coupling, said tapered coupling forming a smooth transition to an outer diameter of the insulated wire, that is easy to insert and position on the right chambers of the heart. The atraumatic tip prevents tissue damage to the ventricle wall and atrium, and prevents entanglement with and damage to chordae during deployment, adjustment, and withdrawal.

The present disclosure relates to a transvenous intracardiac pacing catheter having improved leads, and particularly to devices, methods, and systems for establishing and maintaining atrio-ventricular (AV) synchrony in a patient by providing an insertable atrio-ventricular sequential pacing catheter system having an inner ventricular sheath disposed within a central axial conduit (lumen) of an atrial sheath. The ventricular sheath houses three (3) ventricle leads, including a distal lead and two ventricular wall leads. The atrial sheath has four (4) perimeter conduits (lumens) and a central axial conduit. The four perimeter conduits (lumens) housing the atrium leads for delivery to the atrium. The central axial conduit (lumen) for delivering the ventricular sheath to the ventricle, as part of a two-step sequence, whereby the ventricle leads are extended/delivered to the ventricle when the ventricular sheath is withdrawn, and whereby the atrium leads are then extended/delivered to the atrium by withdrawing the atrial sheath proximally towards the outer steerable delivery catheter and connector assembly.

In a preferred embodiment, there are seven stainless steel or nitinol lead wires with a polymer insulation, e.g. parylene coating, polytetrafluoroethylene (PTFE), and radiopaque tips. Four of the lead wires are leads for the atrium, two of the lead wires are for the ventricle, and one of the lead wires forms the distal tip. The atrial lead wires are incorporated into a four+one (4+1) lumen extrusion. The ventricular and distal lead wires are incorporated into a three lumen "stoplight" extrusion. The ventricular three lumen "stoplight" extrusion is disposed within a central axial lumen or conduit of the atrial sheath. The assembly fitted into correct position using fixtures. In a preferred embodiment, the lead wires are exposed sequentially by withdrawing the sheaths. In another preferred embodiment, the lead wires are configured with a shape and materials to reduce endothelial injury, and increase performance. In a preferred embodiment, the connector assembly attached the lead wires to plugs for connection to the pulse transmission unit.

BRIEF DESCRIPTION OF THE DRAWINGS

FIG. 18 is a chart of an acute first in human study and is useful to support an embodiment of the present invention. This figure shows an example study of a sample of 10 patients, although not necessarily for any specific indication. This figure illustrates that the device is positioned and deployed in an average of 1 minute with fluoroscopy guidance and once vascular access, internal jugular is obtained. After deployment, catheterization and testing takes about 24 minutes to perform a diagnostic left heart catheterization and test the device as described, including to position and deploy the device, pace the RV, pace the A synchronize AV pacing, perform a left side diagnostic, and the pace the RV, pace the A, synchronize the AV pacing, and remove the device, according to the invention.

FIG. 19 is an example of a chart of data in an embodiment of the invention from a procedure recording a non-limiting preferred embodiment. This figure shows by subject and lead, the impedance, the threshold, and the current, recorded. This shows safe delivery with and without fluoroscopic guidance, successful pacing, excellent contact and hold of the leads against the cardiac tissue, with no adverse events or significant adverse events at discharge, according to the invention.

FIG. 35 is a flowchart showing a sequential process for deploying and optionally calibrating the leads.

DETAILED DESCRIPTION

Figure 1:
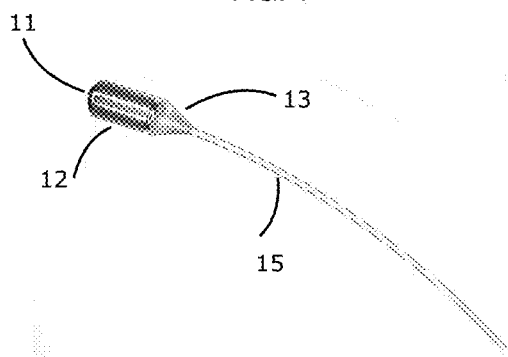
FIG. 1 is an illustration of one embodiment of an optimized lead having a shape and constructed of materials to reduce endothelial injury and maximize energy transfer and signal transduction, according to the invention.

Disclosed embodiments are directed to a self-positioning, quick-deployment low profile transvenous electrode system for sequentially pacing both the atrium and ventricle of the heart in the "dual chamber" mode, comprising a plurality of insulated electrical wires bundled together to form at least two in-line sets of leads is disclosed. The invention provides an emergency pacemaker that will pace and sense both atrial and ventricular chambers and provide "dual chamber" control of the heart using a lead that can be safely and easily inserted into the heart in an emergency situation. "Dual chamber" pacing refers to continuous monitoring of the spontaneous activity of the heart both in the atria and in the ventricles, interpreting the detected events according to certain accepted algorithms and providing stimuli to the chambers as needed to maintain a physiologically appropriate rhythm. Importantly, the device can be deployed with and without fluoroscopic guidance. In one embodiment, a self-positioning feature allows the device to be used without the extensive training and specialist experience that has been historically required for pacing devices.

In some embodiments of the invention, the device comprises three (3) ventricular leads and four (4) atrial leads, made from shape memory material. Two of the three ventricular leads are bent at 90 degrees from the central axial lead and are 180 degrees from each other. The four atrial leads are bent at 90 degrees from the central axis (x-axis), and are each separated 90 degrees from the adjacent leads, in the y-axis plane.

In some embodiments of the invention, both sets of leads are mounted and contained inside a slender e.g. 8Fr (1 mm), tubular, flexible elongated e.g. 35 cm retaining sheath that serves as a guide and delivery system during insertion and removal of the electrode system. Each of the wires is surrounded individually by electrical insulation.

In some embodiments of the invention, the bundle of insulated wires can be arranged in either a parallel or helical configuration. In order to conform to heart chambers of different sizes, the leads will be produced in different lengths and appropriate distances between the electrodes.

In some embodiments of the invention, the electrode system is constructed by assembling a plurality of insulated superelastic electrically conductive wires. The insulation material separates each of the wires from each other, but the wires are mounted in a bundle as a single cable-like structure. At the proximal end, the electrodes are connected to an external pacemaker. At the distal end, the individual wires once inserted into the heart will make contact with either atrial or ventricular tissue. The distal ends of the individual wires may include spherical electrode contacts that will make contact with atrial tissue or ventricular tissue.

In some embodiments of the invention, each of the wires has memory and is pre-formed in a specific curvature but also is resilient enough to be contained in the sheath prior to being positioned within the heart chambers. Since both sets of leads for the ventricle and the atrium are contained inside a single slender flexible retaining sheath that is the guide and delivery system during insertion and removal of the electrode system, the ventricular electrode or electrodes which can be pacemaker sensors or stimulators are released first after the retaining sheath has been successfully inserted into the right ventricle. At this point, the sheath is retracted allowing the ventricle wire leads to escape from the sheath and because of each wire's pre-formed shape which has memory, spread out to individually contact the endocardial surfaces. The leads expand outwardly, engaging the tissue and chamber wall of the ventricle. If a mechanical parallel wire configuration is chosen in the sheath, the wires can be released and make contact in the same plane. Otherwise, the wires can be staggered within the ventricular chamber. If a helical configuration of the wires is chosen in the sheath, the wires are staggered upon release to cover different points of a chamber wall. Ideal wires for this configuration are disclosed in U.S. Pat. Nos. 6,137,060 and 3,699,886.

Continued retraction of the sheath will then allow the escape of the atrial wires and electrodes which also have memory and which, upon escape from the sheath, will proceed outwardly towards the atrial tissue for engagement.

As discussed above, in some embodiments of the invention, the distal ends of the individual wires may have spherical conductive ball tips to provide high current density and sensitivity. For the physician to effectively introduce the device transvenously, the sheath will have to be extended all the way forward initially such that it covers all the wires with the possible exception of the distal electrodes, which may protrude beyond the sheath during the introduction of the sheath with the conducting leads into the heart. The path of the sheath with the leads during insertion is into the subclavian or jugular vein past the atrium and into the ventricle. Once the electrode system reaches the apex of the right ventricle, the operator begins to pull back slowly on the sheath, thus releasing each wire individually until all necessary contact points are made.

In some embodiments of the invention, each lead wire is made of stainless steel, or a superelastic or memory shape retention material such as Nitinol™, and as the sheath is slowly pulled back the lead wires are released. Each lead wire will be pre-shaped with the proper orientation so that as the medical personnel, e.g. cardiac interventionalists, emergency medical technicians, surgical staff, outpatient staff, etc., pulls the sheath back, the wire fans outwardly until the lead wire tips rest against the interior wall of each chamber, thus making electrical contact. The memory in the lead wire will hold it in place within the chamber. The ball tip ending of each lead wire as well as the highly flexible chosen material will minimize trauma to the endocardium while allowing a sufficiently large surface area for electrical conduction.

Biocompatible Materials

Any of the devices and/or components thereof, including the lead wires, may be fabricated from any suitable biocompatible material or combination of materials. For example, an outer chassis, and/or components thereof may be fabricated from biocompatible materials, metals, metal alloys, polymer coated metals, and/or the like. Suitable biocompatible materials, metals and/or metal alloys can include polymers, co-polymers, ceramics, glasses, aluminum, aluminum alloys, stainless steel (e.g., 316 L stainless steel), cobalt chromium (Co—Cr) alloys, cobalt chromium molybdenum (Co—Cr—Mo) alloy, cobalt chromium nickel molybdenum (Co—Cr—Ni—Mo) alloy, nickel-titanium alloys (e.g., Nitinol®), and/or the like. Moreover, any of the chassis or components may be covered with a suitable polymer coating, and can include parylene-based polymers, parylene N, parylene C, parylene D, polytetrafluoroethylene (PTFE), ethylenetetrafluoroethylene (ETFE), polyimide, natural or synthetic rubber, polyethylene vinyl acetate (PEVA), polybutyl methacrylate (PBMA), translute Styrene Isoprene Butadiene (SIBS) copolymer, polylactic acid, polyester, polylactide, D-lactic polylactic acid (DLPLA), polylactic-co-glycolic acid (PLGA), and/or the like.

Any of the lead wires may also be fabricated from any suitable biocompatible material or combination of materials selected from solid or braided metal wire, wire with a first metal core (solid or braided) and a second metal outer shell layer (solid or braided), and combinations thereof.

In order for the electrode system within the sheath to freely navigate through the blood vessels, it must have a very smooth surface. Adequate flexibility must be achieved with materials that do not fracture or fail prematurely. The insulation material used to insulate each individual wire will be of the type used in the production of existing pacing leads. Furthermore, the sheath material used will be a thermoplastic elastomer similar to those used in the manufacture of catheters and for added strength it can be braided.

In one non-limiting embodiment, the electrode system in accordance with this invention may be designed primarily for emergency temporary use such that the leads described have passive fixation. However, in another non-limiting example, it is possible that the present invention can be utilized as part of a permanently implanted pacemaker system such that the electrode would become embedded in the heart tissue or actively attached to the endocardium by one of many means available for active fixation.

Some biocompatible synthetic material(s) can include, for example, polyesters, polyurethanes, polytetrafluoroethylene (PTFE) (e.g., Teflon), and/or the like. Where a thin, durable synthetic material is contemplated (e.g., for a covering), synthetic polymer materials such as parylene-based materials, expanded PTFE or polyester may optionally be used. Other suitable materials may optionally include elastomers, thermoplastics, polyurethanes, thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene (LDPE), high-density polyethylene (HDPE), ultra-high density polyethylene (UHDPE), polyolefins, polyethylene-glycols, polyethersulphones, polysulphones, polyvinylpyrrolidones, polyvinylchlorides, other fluoropolymers, polyesters, polyethyleneterephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), PTFE, elongated PTFE, expanded PTFE, siloxane polymers and/or oligomers, and/or polylactones, and block co-polymers using the same.

Radiopaque Materials

Barium Sulfate. Barium sulfate (BaSO4) is a radiopaque material widely compounded in medical formulations and a common filler used with medical-grade polymers. It is an inexpensive material, costing approximately $2/lb; and its white color can be changed with the addition of colorants.

With a specific gravity of 4.5, barium sulfate is generally used at loadings of 20 to 40% by weight. While a 20% barium sulfate compound is typical for general-purpose medical device applications, some practitioners prefer a higher degree of radiopacity than can be provided by that loading. With striped tubing, for example, a 40% compound is standard.

A loading of 20% barium sulfate by weight is equivalent to about 5.8% by volume; 40% by weight equals 14% by volume. As the barium content moves beyond about 20% by volume, compounds begin to show losses of the base polymer's tensile strength and other mechanical properties. It is therefore best to formulate radiopacifiers at the minimum level for each application; excessive use of these fillers is not recommended.

Bismuth. Considerably more expensive than barium at $20 to $30/lb (depending on the chemical salt selected), bismuth compounds are also twice as dense. Bismuth trioxide ($Bi_2O_3$), which is yellow in color, has a specific gravity of 8.9; bismuth subcarbonate ($Bi_2O_2CO_3$) has a specific gravity of 8.0; and bismuth oxychloride (BiOCl) has a specific gravity of 7.7. Because of the density, a 40% bismuth compound contains only about half the volume ratio as a 40% barium sulfate compound. Since bismuth produces a brighter, sharper, higher-contrast image on an x-ray film or fluoroscope than does barium, it is commonly used whenever a high level of radiopacity is required.

Compared with barium, higher loadings are also possible: even a 60% bismuth compound can maintain the same base polymer mechanical properties as a 40% barium sulfate compound. A 20% bismuth loading by weight equals 3% by volume; a 40% loading by weight equals 7.6% by volume. Bismuth is sensitive to compounding and must be treated gently, with low-shear mixing recommended for optimum results. Bismuth provides high levels of radiopacity.

Tungsten. A fine metal powder with a specific gravity of 19.35, tungsten (W) is more than twice as dense as bismuth and can provide a high attenuation coefficient at a cost of approximately $20/lb. A loading of 60% tungsten has approximately the same volume ratio as a 40% bismuth compound. Devices can be made highly radiopaque with relatively low loadings of tungsten, enabling good mechanical properties to be maintained. Because of its density, tungsten is typically selected as a filler for very-thin-walled devices.

A 50% tungsten loading by weight equals only 5.4% by volume; an 80% loading by weight represents 18.5% by volume. Tungsten is black in color, which cannot be changed with colorants. It is abrasive and can cause accelerated wear in extruders and other processing equipment. Devices filled with high loadings of tungsten will exhibit surface roughness. Because the material invites oxidation in the presence of oxygen and heat and is highly flammable, care should be taken while drying it. With elastomers, barium sulfate mixes better than do tungsten or bismuth compounds.

Compounding Considerations

Newer x-ray machines generally operate at higher energy levels than older ones—typically at 80 to 125 kVp as compared with 60 to 80 kVp for older machines. Higher energy radiation increases the transmission of photons and can require higher levels of radiopacity to provide the desired attenuation. Therefore, devices produced with barium sulfate compounds might not appear as bright on newer machines, for which bismuth compounds would be a better choice of radiopaque filler. Blending these materials, however, can often be the best solution, especially for multipurpose formulations used over a broad range of energy levels. A blend of barium, easily attenuated at low energy levels, and bismuth, attenuated at higher levels, often works well.

Compounding radiopaque materials includes factoring in the degree of attenuation of the device, the tensile strength, elongation, and other mechanical properties of the polymers. Fillers, antioxidants, stabilizers, and colorants may also be included with metallic fillers.

Delivery

The present invention can be used in emergency rooms, after open heart surgery, during or after minimally invasive heart surgery or implant procedures such as valve repair or replacement, in intensive care units, at the bedsides, cardiac catheterization labs, ambulances, battle fields and other emergency settings where patients with heart block or other life threatening arrhythmias may be found.

The term "quick" or "quickly" refers to the aspect of the invention that the electrode system can be deployed in a short amount of time. In a preferred embodiment, the electrode system can be deployed within a patient in approximately 1 minute. In another preferred embodiment, the electrode system can be deployed within a patient in approximately 1-5 minutes. In another preferred embodiment, the electrode system can be deployed within a patient in approximately 1-15 minutes. In another preferred embodiment, the electrode system can be deployed within a patient in approximately 1-20 minutes. In another preferred embodiment, the electrode system can be deployed within a patient in approximately 1-25 minutes. In another preferred embodiment, the electrode system can be deployed within a patient in less than 25 minutes. In another preferred embodiment, the electrode system can be deployed within a patient in less than 15 minutes. In another preferred embodiment, the electrode system can be deployed within a patient in less than 5 minutes. In another preferred embodiment, the electrode system can be deployed within a patient in less than 3 minutes.

Independent Claims

In a preferred embodiment, the invention provides an electrode system connectable to a pacemaker for sequentially pacing both the atrium and ventricle of a human heart comprising: a plurality of insulated electrical leads comprising a first set of ventricle leads and a second set of atrium leads, each said lead having an insulated wire and an atraumatic tip, said atraumatic tip comprising a domed head connected to a cylindrical sidewall, said cylindrical sidewall having a sloped proximal edge connected to a tapered coupling, said tapered coupling forming a smooth transition to an outer diameter of the insulated wire, a ventricular sheath disposed over said first set of ventricle leads, the ventricular sheath being retractable from the ventricle leads to deploy the ventricle leads in the ventricle, each of the ventricle leads having a resiliency and shape to be deployed in contact with the ventricle wall when the ventricular sheath is retracted therefrom, an atrial sheath disposed over said second set of atrium leads and the ventricular sheath disposed within the atrial sheath along a central axis, the atrial sheath being retractable from the atrium leads to deploy the atrium leads in the atrium, each of the atrium leads having the resiliency and shape to be deployed in contact with the atrium wall when the atrial sheath is retracted, wherein the ventricle leads are not attachable to the ventricle wall, but are adapted to contact the ventricle wall, and the atrium leads are not attachable to the atrium wall, but are adapted to contact the atrium wall.

In another preferred embodiment, the invention provides a method for quickly deploying a cardiac pacing device to a heart in a patient, comprising: (i) Providing the system herein; (ii) Accessing a jugular vein in the patient and advancing the catheter sheath under ultrasound or other non-fluoroscopic imaging modality to a right ventricle of the heart of the patient; (iii) Withdrawing the outer catheter sheath to a first position to deploy the first set of three ventricle leads; (iv) Withdrawing the outer catheter sheath to a second position to deploy the second set of four atrium leads; (v) Performing a diagnostic test using the first set of three ventricle leads and the second set of four atrium leads to identify patient cardiac patterns and to validate the operation of the system; (vi) Performing a cardiac pacing routine appropriate as a treatment for the patient cardiac pattern using the system.

Ventricle Only

In another embodiment, the invention provides a self-positioning, quick-deployment low profile transvenous electrode system for pacing of a heart with a pacemaker, comprising: a pair of insulated electrical wires to form a first ventricle lead and a second ventricle lead, the first and the second ventricle leads disposed within an outer steerable catheter sheath, said outer steerable catheter sheath being removable from said first and said second ventricle leads when inserted into the heart for deploying the first ventricle lead and the second ventricle lead to the ventricle, said outer steerable catheter sheath being entirely removed from the ventricle when the transvenous electrode system is engaged, each of the first and the second ventricle leads have a proximal body portion, a distal end portion, and a tip portion, the proximal body portion made from a radiopaque polymer-covered copper wire, the distal end portion made from shape memory material, the shape memory material selected from stainless steel, spring steel, cobalt-chromium alloy, nickel-titanium alloy, and mixtures thereof, the tip portion comprising a domed head connected to a cylindrical sidewall, said cylindrical sidewall having a sloped proximal edge connected to a tapered coupling, said tapered coupling forming a smooth transition to an outer diameter of the insulated wire, the tip portion made from shape memory material and a radiopaque material, the radiopaque material selected from a barium-containing compound, a bismuth-containing compound, a steel compound, a tungsten-containing compound, and mixtures thereof, the two ventricle leads are offset 180 degrees from each other, the steerable catheter sheath is about 1.3 mm diameter or 4 French and is comprised of a distal portion and a proximal portion, and has a distance marker every 10 cm along its entire length, the distal portion of the steerable catheter sheath is 5 cm in length and has a 0.010" pitch coil and a biocompatible polymer cover, the proximal portion of the steerable catheter sheath is 30 cm in length, has a 0.020" pitch coil, a biocompatible polymer cover, at a proximal end of the proximal portion has a hub element, a Touhy-Borst access connector with a side port, an actuator dial that allows the steerable catheter sheath to be shaped and controlled, a deployment stop, and a cable junction housing.

Ventricle and Atrium Leads

Any of the embodiments herein may include wherein the first set comprises three ventricle leads and the second set comprises four atrium leads.

Any of the embodiments herein may include wherein the electrode system is configured for withdrawal from the heart so that the atrium leads are returnable to the atrial sheath and the ventricle leads are returnable to the ventricular sheath at a location above the SVC-RA junction.

Any of the embodiments herein may include wherein the atraumatic tip includes a metal portion comprised of stainless steel, nickel-titanium alloy, gold, platinum, or iridium.

Any of the embodiments herein may include wherein the atrium leads are the same length or different staggered lengths, having a pre-set curved shape, and extend about 2.00 inches from a central axis of the atrial sheath.

Any of the embodiments herein may include wherein the ventricle leads comprise a straight distal ventricle lead and two pre-set curved shape ventricle leads, the ventricle leads are the same length or different staggered lengths, the straight distal ventricle lead extending along a central axis of the atrial sheath, and the two pre-set curved shape ventricle leads extend about 1.50 inches from the central axis of the atrial sheath.

Any of the embodiments herein may include wherein the atrium leads having a length of about 3.14 inches (½C=pi/2*D), having a pre-set curved shape, and extend about 2.00 inches from a central axis of the atrial sheath.

Any of the embodiments herein may include wherein the ventricle leads comprise a distal ventricle lead and two pre-set curved shape ventricle leads, the distal ventricle lead having a length of about 2.76+/−0.20 inches extending along a central axis of the atrial sheath, and the two pre-set curved shape ventricle leads having a length of about 2.355 inches (½C=pi/2*D) extend about 1.50 inches from the central axis of the atrial sheath.

Any of the embodiments herein may include wherein when deployed in the ventricle, one of said ventricle leads is a distal ventricle lead extending along a central axis of the atrial sheath, and two ventricle leads are memory shape-set at 90 degrees to the central axis and are offset 180 degrees from each other in a plane perpendicular to the distal ventricle lead.

Any of the embodiments herein may include wherein when the atrium leads are deployed in the atrium, the atrium leads are memory shape-set at 90 degrees to a central axis of the atrial sheath and offset 90 degrees from each other in a plane perpendicular to the central axis.

Any of the embodiments herein may include where the atrium leads and the ventricular leads have different lengths.

Steerable Delivery Catheter

Any of the embodiments herein may include having a steerable delivery catheter with a female Luer connector, a side-port Tuohy Borst access connector, a deployment stopper, a terminal connection connected to the electrical leads, and an extension hub, the atrial sheath disposed within the steerable delivery catheter, the ventricular sheath disposed within the atrial sheath.

Any of the embodiments herein may include wherein the steerable delivery catheter has an inner PTFE liner, a Tie layer, a braid, an outer jacket, and a heat shrink fusing sleeve located near a distal tip.

Any of the embodiments herein may include wherein the steerable delivery catheter has an outer diameter (OD) of 0.104+−0.003 inches, an inner diameter (ID) of 0.090+−0.002 inches, and a working length of 12.00+−0.30 inches.

Any of the embodiments herein may include wherein the female Luer connector has a connector orientation that is keyed to a leads orientation of the electrical leads, wherein the connector orientation informs an operator of the leads orientation.

Any of the embodiments herein may include wherein the steerable delivery catheter has a dead-stop marker to indicate a maximum safe distance of insertion of the electrical leads.

Any of the embodiments herein may include wherein the ventricular sheath comprises a stoplight extrusion having three (3) conduits (lumens), the inner diameter of the three conduits (lumens) configured to deliver the ventricular leads.

Any of the embodiments herein may include wherein the atrial sheath comprises a 4-in-1 extrusion having a central axial conduit (lumen) and four perimeter conduits (lumens), the inner diameter of the central axial conduit (lumen) configured to deliver the ventricular sheath, and the inner diameter of the four perimeter conduits (lumens) configured to deliver the atrial leads.

Any of the embodiments herein may include wherein the atrial sheath and the ventricular sheath have radio-opaque distance markers.

Polarity

Any of the embodiments herein may include wherein the electrical leads are monopolar, either positive or negative polarity.

Any of the embodiments herein may include wherein when connected to a pacemaker, the distal ventricle lead and a second ventricle lead have a signal of a first polarity, and a third ventricle lead has a signal of an opposite polarity.

Any of the embodiments herein may include wherein when connected to a pacemaker, two of the atrium leads have a signal of a first polarity and two of the atrium leads have a signal of an opposite polarity.

Cross-Talk

Any of the embodiments herein may include wherein the insulated wire of each of the atrium leads and the ventricle leads are radio-opaque, comprised of PTFE or PTE, and prevent cross-talk.

Atraumatic Tip

Any of the embodiments herein may include wherein the atraumatic tip of the atrium leads and the ventricle leads are the same size or different.

Any of the embodiments herein may include wherein the atrium leads each have an atraumatic tip with an outer diameter of 8 Fr (8×0.33 mm=2.64 mm=0.1039 in).

Any of the embodiments herein may include wherein at least two of the ventricle leads each have an atraumatic tip with an outer diameter of 8 Fr (8×0.33 mm=2.64 mm=0.1039 in).

Any of the embodiments herein may include wherein one of the ventricle leads is a distal ventricle lead and has an atraumatic tip with an outer diameter of 11 Fr (11×0.33 mm=3.63 mm=0.1429 in).

Any of the embodiments herein may include wherein the insulated wire has a parylene coating. Any of the embodiments may include along at least a part thereof, a polymer, including without limitation parylene, doped with a releasable anti-coagulant drug or anti-inflammatory drug.

Any of the embodiments herein may include wherein each of said electrical leads has a proximal portion made from wire with a radio-opaque material and a distal portion made from a shape memory material.

Any of the embodiments herein may include wherein each of said atraumatic tips has a radio-opaque material.

Any of the embodiments herein may include wherein the ventricular sheath and atrial sheath are each made from a polymer that is doped in at least one segment with a radiopaque material to form a radiopaque polymer sheath, each of the ventricle and atrium leads have a proximal body portion, a distal end portion, and the atraumatic tip, the proximal body portion made from a radiopaque polymer-covered copper wire, the distal end portion made from shape memory material, the shape memory material selected from stainless steel, spring steel, cobalt-chromium alloy, nickel-titanium alloy, and mixtures thereof, the atraumatic tip made from a pulse transmitting material and a radiopaque material, the radiopaque material selected from a barium-containing compound, a bismuth-containing compound, a steel compound, a tungsten-containing compound, and mixtures thereof, two of the three ventricle leads are memory shape-set at a 90 degree angle in an expanded configuration, and the two ventricle leads are offset 180 degrees from each other, one of the three ventricle leads is a distal ventricle lead extending along a central axis of the atrial sheath, each of the four atrium leads are memory shape-set at a 90 degree angle in an expanded configuration, and each of the four atrium leads are separated 90 degrees from each other, the atrial sheath and the ventricle sheath are each comprised of a distal portion and a proximal portion, and each has a distance marker every 10 cm along its entire length.

Pacemaker

Any of the embodiments herein may include wherein the atrium leads and the ventricle leads each connect to lead terminals that extend from a cable junction housing to a pacemaker, wherein the pacemaker comprises computer program instructions readable by a processor to provides functions selected from the group consisting of: a diagnostic function, a sensor operation, a stimulation signal, a program for an individual lead for sensing, a program to reduce over-sensing of the ventricular leads by T-waves or other noise or attenuating or interfering signals, a program to reduce over-sensing of the atrium leads by the R-wave, a program to minimize cross-talk, and a program to adjust sensing and stimulation on a lead-by-lead basis.

Any of the embodiments herein may include wherein the atrium leads are memory shape-set to sense and stimulate an atrial endothelium and the ventricle leads are memory shape-set to sense and stimulate an ventricular endothelium.

Any of the embodiments herein may include wherein each of said ventricle leads is connected to a ventricular sensor or stimulator in a pacemaker and each of said atrium leads is connected to an atrium sensor or stimulator in said pacemaker.

Any of the embodiments herein may include wherein the electrical leads are connected to a pacemaker that includes two sequential pulse generators to provide sensing and stimuli for a ventricle and for an atrium for sequentially pacing both the atrium and ventricle of a heart in the "dual chamber" mode.

Any of the embodiments herein may include wherein the pacemaker includes computer program instructions executable by a processor for performing digital signal processing for the ventricle leads and the atrium leads, wherein the digital signal processing is selected from the group consisting of: multiple input, multiple output (MIMO), single input multiple output (SIMO), single input single output (SISO), and multiple input single output (MISO).

Any of the embodiments herein may include wherein the computer program instructions executable by a processor provides one or more functions selected from: decreasing sensitivity of certain leads and increasing sensitivity of other leads during a depolarization cycle (PQRST) allows the invention to increase SNR in the sensing function, decreasing or increasing stimulatory signals to one or more leads allows the invention to more accurately provide stimulation to cardiac tissue to provide a level of granularity to the stimulation function, programming leads so that sensing leads are not required to share the function of a shocking/stimulation leads, and bypassing damaged or degraded leads to allow continued functioning without requiring the entire device to be removed from a patient, this increasing the longevity of implanted devices using the inventive technology.

Variations

Any of the dual chamber embodiments herein may include wherein the pacemaker includes two sequential pulse generators that can provide sensing and stimuli for a ventricle and an atrium for sequentially pacing both the atrium and ventricle of a heart in the "dual chamber" mode.

Any of the embodiments of the present invention may include 4 atrial, and 3 ventricular wires in a configuration where the atrial are 90 degrees from each about a Y-axis, and where the ventricular are in a planar configuration that is perpendicular to the central X-axis.

Any of the embodiments of the present invention may include wherein the atrial leads and ventricle leads have uninsulated wire in certain locations.

Any of the embodiments of the present invention may include wherein the copper body portion is braided or bonded to the distal end portion, where the distal end portion is steel or NiTi alloy.

Any of the embodiments of the present invention may include wherein the shape-setting of the atraumatic tip is performed at the same time as the shape-setting of the wire portion of the leads.

Any of the embodiments of the present invention may include wherein the shape-setting is performed faster by changing the wire cross section.

Any of the embodiments of the present invention may include wherein the atraumatic tip is a composite of a shape memory material and a radiopaque material.

Any of the embodiments of the present invention may include wherein the radiopaque materials are Tungsten, Barium, and/or Bismuth compounds. In particular, Bismuth provides a brighter luminescence under Xray. Bismuth compounds include $Bi_2O_3$, $Bi_2O_2CO_3$, and BiOCl. Barium sulfate provides excellent compounding with polymer coatings, such as polyimides. Barium radiopaque polymers may be used for the catheter sheath/jacket, eyelet, as an RO band, and on other electrode portions, and sheath portions.

Any of the embodiments of the present invention may include wherein the polymer is polyimide, or where the polymer is silicone plus a lubricity agent, is made from PebaSlix 35D, is made from Pebax 72D, and the like.

Any of the embodiments of the present invention may include wherein the sheath is configured to provide a 90 degree curve over a 2.5" diameter bend, and is also configured to provide a hockey-stick bend at a 45 degree angle+/−5 degrees.

Any of the embodiments of the present invention may alternatively include wherein the lead wires are unipolar or bipolar. Any of the embodiments of the present invention may alternatively include wherein the lead wires are solid wire, braided wire, coaxial with an inner conductor and outer insulator, and/or co-radial with two parallel helically coiled wires. Any of the embodiments of the present invention may alternatively include wherein the lead wires are composite having a low-resistance inner metal such as stainless steel or silver, and a high-strength outer shell metal such as nickel-titanium alloy, titanium, stainless steel, and platinum alloy. Any of the embodiments of the present invention may alternatively include wherein the polymer insulation is parylene, polytetrafluoroethylene (PTFE), ethylenetetrafluoroethylene (ETFE), polysiloxane, HP silicone, ETR silicone, poly(ether)urethane, and copolymer hybrid composites configured to have strength, lubricity, abrasion resistance, flexibility, and biostability for use as lead wire electrode insulation. Any of the embodiments of the present invention may alternatively include wherein the lead wire tip may be configured with a textured surface, a mesh surface, a metal foam surface, a micro-perforated surface, or sintered metal wire mesh surface.

Computer Programs

In another preferred embodiment, the invention provides wherein the invention includes computer program instructions executable on a processor for performing one or more functions selected from: decreasing sensitivity of certain leads and increasing sensitivity of other leads during a depolarization cycle (PQRST) allows the invention to increase SNR in the sensing function, decreasing or increasing stimulatory signals to one or more leads allows the invention to more accurately provide stimulation to the atrial endothelium and the ventricular endothelium. In an alternate embodiment, the sensing and stimulation may be directed to cardiac tissue to provide a level of granularity to the stimulation function, programming leads so that sensing leads are not required to share the function of a shocking/stimulation leads, and bypassing damaged or degraded leads to allow continued functioning without requiring the entire device to be removed from a patient, this increasing the longevity of implanted devices using the inventive technology.

Methods

In another preferred embodiment, the invention provides a method for quickly deploying a cardiac pacing device to a heart in a patient, comprising:
(i) Providing the transvenous, dual-chamber dual-lumen system claimed and described herein;
(ii) Accessing a jugular vein in the patient and advancing the catheter sheath under ultrasound or other non-fluoroscopic imaging modality to a right ventricle of the heart of the patient;
(iii) Withdrawing the outer steerable catheter sheath to a first position to expose the first inner sheath and the second inner sheath;
(iv) Withdrawing the first inner sheath to a second position to expose and actuate the ventricle leads to connect with the ventricle tissue;
(iv) Withdrawing the second inner sheath to a third position to expose and actuate the atrium leads to connect with atrium tissue;
(v) Performing a diagnostic test to identify the patient cardiac patterns and to validate the operation of the system;
(vi) Performing a cardiac pacing routine appropriate as a treatment for the patent cardiac pattern;
(vii) Removing the catheter sheath and allowing the system to remain within the patient;
wherein performing steps (i)-(iv) are performed in a time period no longer than 3-5 minutes or 3-10 minutes, and steps (v)-(vii) are performed in a time period from 1 hour up to 7 days.

In another preferred embodiment, the invention provides, wherein performing steps (i)-(vii) are performed in a time period no longer than 30 minutes.

In another preferred embodiment, the invention provides, wherein performing steps (i)-(iv) are performed in a time period no longer than 3-5 minutes.

In another preferred embodiment, the invention provides, wherein the system is deployed in a patient for a time period from 1 hour up to 7 days of use.

In another preferred embodiment, the invention provides a transvenous electrode system for heart block use in an emergency situation that is low cost, safe and reliable for pacing both the atrium and ventricle chambers of the heart of a patient with a heart block.

In another preferred embodiment, the invention provides an emergency heart pacemaker that requires only a small incision to insert the lead that will provide dual chamber (sequential) pacing and sensing for the atrial and ventricles of the heart.

In another preferred embodiment, the invention provides emergency pacemaker that will avoid problems of single chamber ventricular pacing so that the present invention provides for atrial-ventricular synchrony.

Definitions

The terminology used herein is for the purpose of describing particular embodiments only and is not intended to limit the full scope of the claims. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a", "an" and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" includes any and all combinations of one or more of the associated listed items. It should be understood that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

The embodiments herein, and/or the various features or advantageous details thereof, are explained more fully with reference to the non-limiting embodiments that are illustrated in the accompanying drawings and detailed in the following description. Descriptions of well-known components and processing techniques are omitted so as to not unnecessarily obscure the embodiments herein. Like numbers refer to like elements throughout.

The examples and/or embodiments described herein are intended merely to facilitate an understanding of structures, functions, and/or aspects of the embodiments, ways in which the embodiments may be practiced, and/or to further enable those skilled in the art to practice the embodiments herein. Similarly, methods and/or ways of using the embodiments described herein are provided by way of example only and not limitation. Specific uses described herein are not provided to the exclusion of other uses unless the context expressly states otherwise.

Cardiac Electrophysiology

The electrical conduction system of the heart uses Nodal cells and Purkinje cells to maintain synchronization of the atria and the ventricle.

The electrical current is first initiated in the SA node, the hearts natural pacemaker, located at the top of the right atrium. The SA node is composed of nodal cells. In a normal resting adult heart, the SA node initiates firing at 60 to 100 impulses/minute, the impulses causing electrical stimulation and subsequent contraction of the atria. Located at the upper end of the septum, the sinus node creates the synchronized neurally-mediated signal for cardiac pacing.

These signals then travel across the atrium to the atrioventricular node, located close to the septal leaflet of the tricuspid valve. The AV node is also made up of nodal cells and coordinates these incoming electrical impulses.

After a slight delay so the atria can contract and complete ventricular filling, the AV node relays the impulse to Purkinje cells in the ventricle, initially conducted through the Bundle of His which extends along the septum, and which is then divided into the right bundle branch to conduct impulses to the right ventricle and the left bundle branch to conduct impulses to the left ventricle, causing ventricular contraction.

In a healthy heart, the signal flow from the A-V node to the free wall of the left ventricle is rapid to insure the free wall and septum contract in synchrony. For example, a stimulating signal may flow to the free wall in about 70-90 milli-seconds. In patients with conduction abnormalities, this timing may be significantly delayed (to 150 milli-seconds or more) resulting in asynchronous contraction.

In some patients, the conduction path through the Purkinje fibers may be blocked. The location of the block may be highly localized (as in the case of so-called "left bundle branch block" or LBBB) or may include an enlarged area of dysfunctional tissue (which can result from infarction). In such cases, all or a portion of the free wall of the left ventricle is flaccid while the septum is contracting. In addition to contributing to asynchronous contraction, the contraction force of the free wall is weakened.

To address asynchronous contraction, CHF patients can be treated with cardiac pacing of the left ventricle. Such pacing includes applying a stimulus to the septal muscles in synchrony with stimulation applied to the muscles of the free wall of the left ventricle. While infracted tissue will not respond to such stimulus, non-infarcted tissue will contract thereby heightening the output of the left ventricle.

FIGURES

Referring now to the Figures, FIG. 1 is an illustration of one embodiment of an optimized lead having a shape and constructed of materials to reduce endothelial injury and maximize energy transfer and signal transduction, according to the invention. FIG. 1 shows atraumatic tip 10 having domed head 11, cylindrical sidewall 12, sloped proximal edge 13, tapered coupling 14, and insulated wire 15 mounted within aperture 16 (not visible).

Figure 2:
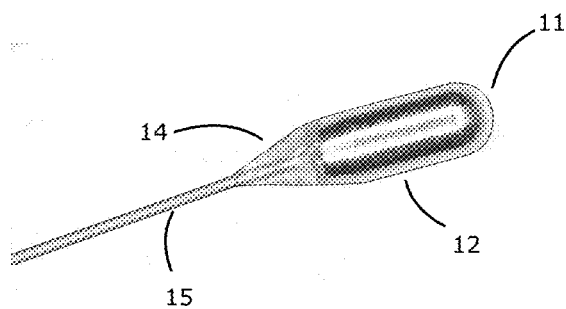
FIG. 2 is an illustration of one embodiment of an optimized lead having a shape and constructed of materials to reduce endothelial injury and maximize energy transfer and signal transduction, according to the invention.

FIG. 2 is an illustration of one embodiment of an optimized lead having a shape and constructed of materials to reduce endothelial injury and maximize energy transfer and signal transduction, according to the invention. FIG. 2 shows domed head 11, cylindrical sidewall 12, tapered coupling 14, and insulated wire 15.

Figure 3:
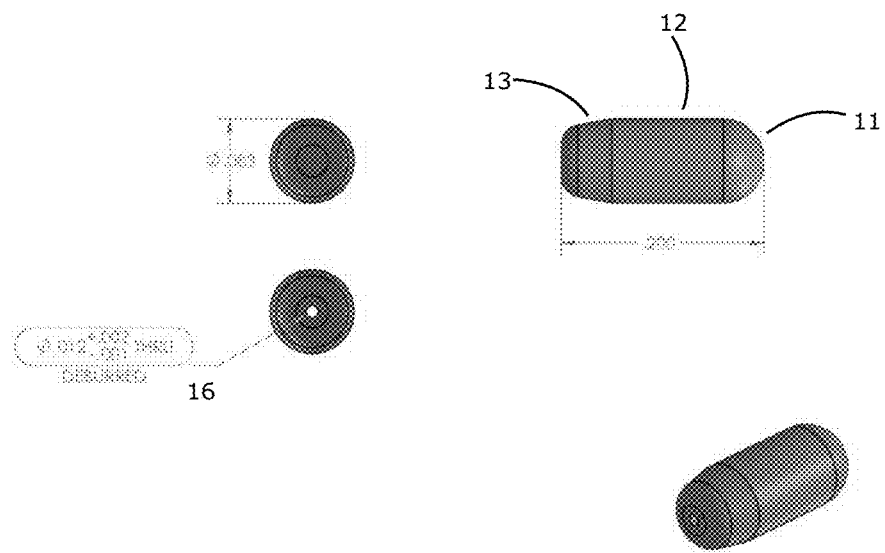
FIG. 3 is an illustration of one embodiment of an optimized tip of a lead having a shape and constructed of materials to reduce endothelial injury and maximize energy transfer and signal transduction, according to the invention.

FIG. 3 is an illustration of one embodiment of an optimized tip of a lead having a shape and constructed of materials to reduce endothelial injury and maximize energy transfer and signal transduction, according to the invention. FIG. 3 shows domed head 11, cylindrical sidewall 12, sloped proximal edge 13, and wire aperture 16.

Figure 4:
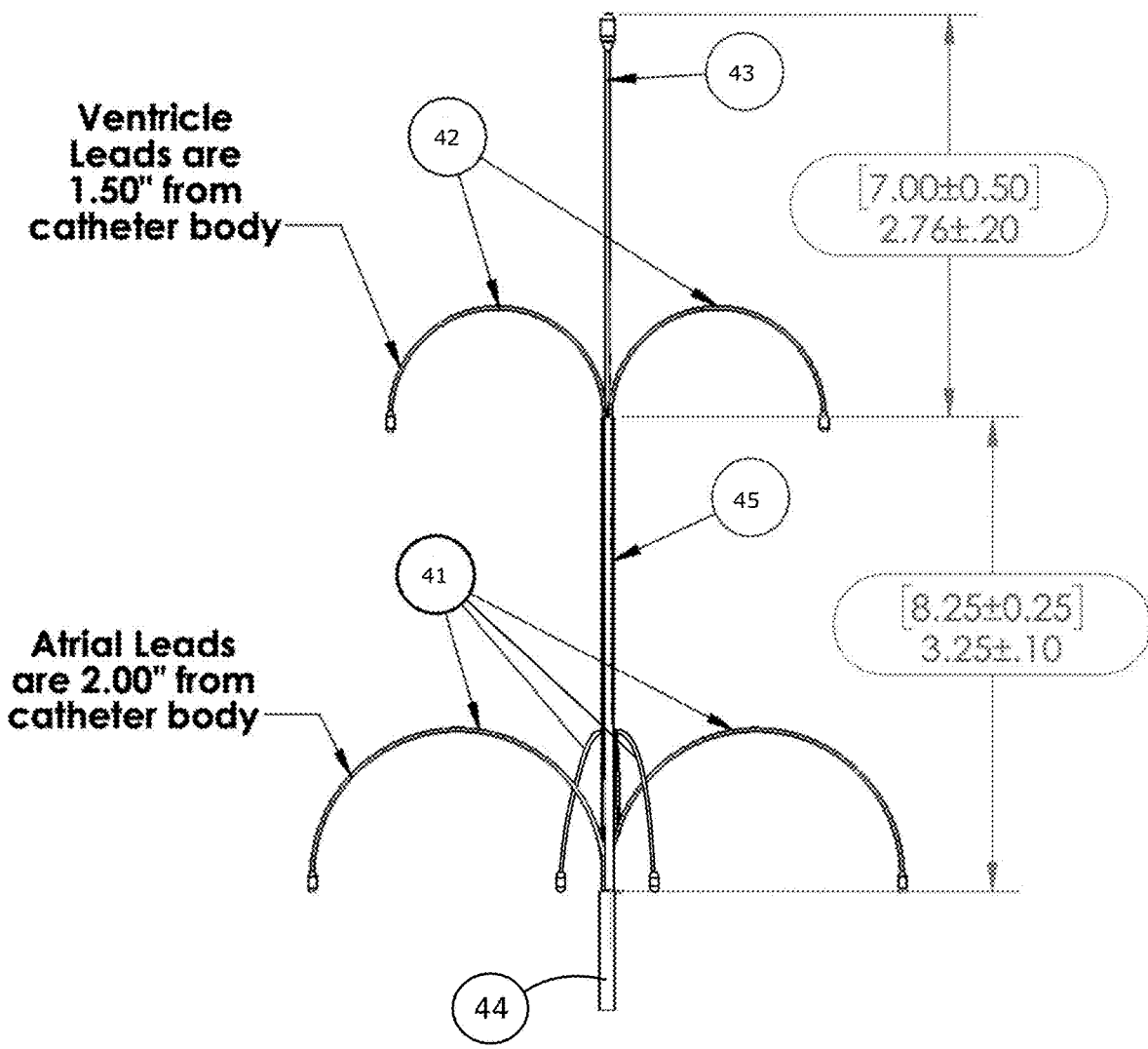
FIG. 4 is an illustration of one embodiment of the deployable intracardiac portion of the device, illustrating the distal lead with rounded capsule tip, the two ventricular leads with rounded capsule tips, the four atrial leads with rounded capsule tips, the retractable ventricular sheath, and the retractable atrial sheath, according to the invention.

FIG. 4 is an illustration of one embodiment of the deployable intracardiac portion of the device, illustrating the distal lead with rounded capsule tip, the two ventricular leads with rounded capsule tips, the four atrial leads with rounded capsule tips, the retractable ventricular sheath, and the retractable atrial sheath, according to the invention. FIG. 4 shows pre-set-curved shape atrium leads 41, pre-set curved shape ventricle leads 42, straight distal ventricle lead 43, atrial sheath 44, and ventricular sheath 45.

Figure 5:
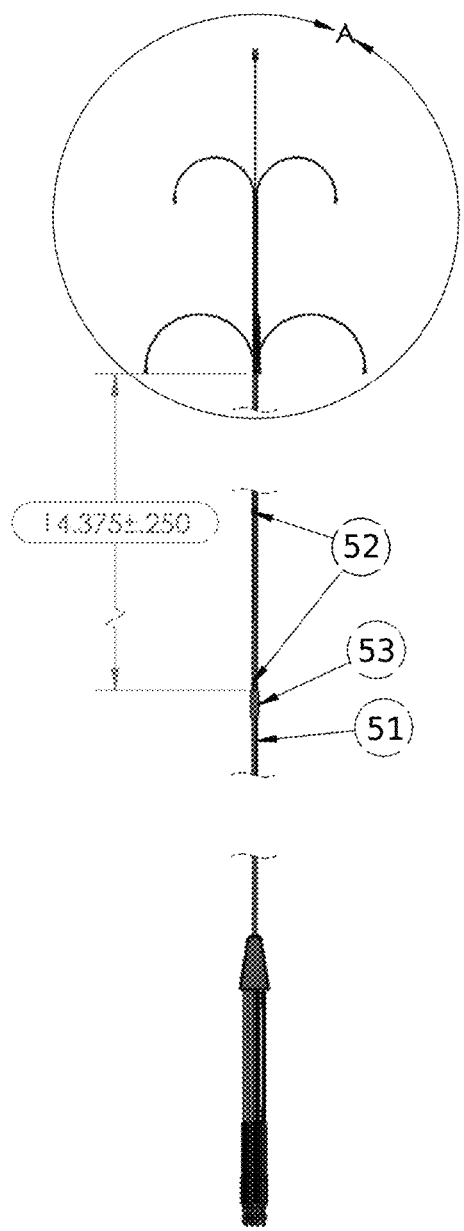
FIG. 5 is an illustration of one embodiment of the deployable intracardiac portion of the device in relation to the intravascular portion/distal extrusion, the proximal extrusion and the external terminal housing portion, illustrating the distal lead with rounded capsule tip, the two ventricular leads with rounded capsule tips, the four atrial leads with rounded capsule tips, the retractable ventricular sheath, the retractable atrial sheath, the proximal extrusion with distance markers and a stopper, the conical wire guide, and the external lead terminals, according to the invention.

FIG. 5 is an illustration of one embodiment of the deployable intracardiac portion of the device in relation to the intravascular portion/distal extrusion, the proximal extrusion and the external terminal housing portion, illustrating the distal lead with rounded capsule tip, the two ventricular leads with rounded capsule tips, the four atrial leads with rounded capsule tips, the retractable ventricular sheath, the retractable atrial sheath, the proximal extrusion with distance markers and a stopper, the conical wire guide, and the external lead terminals, according to the invention. FIG. 5 also shows steerable delivery catheter 51 with atrial sheath 52 and dead stop marker/preventer 53.

Figure 6:
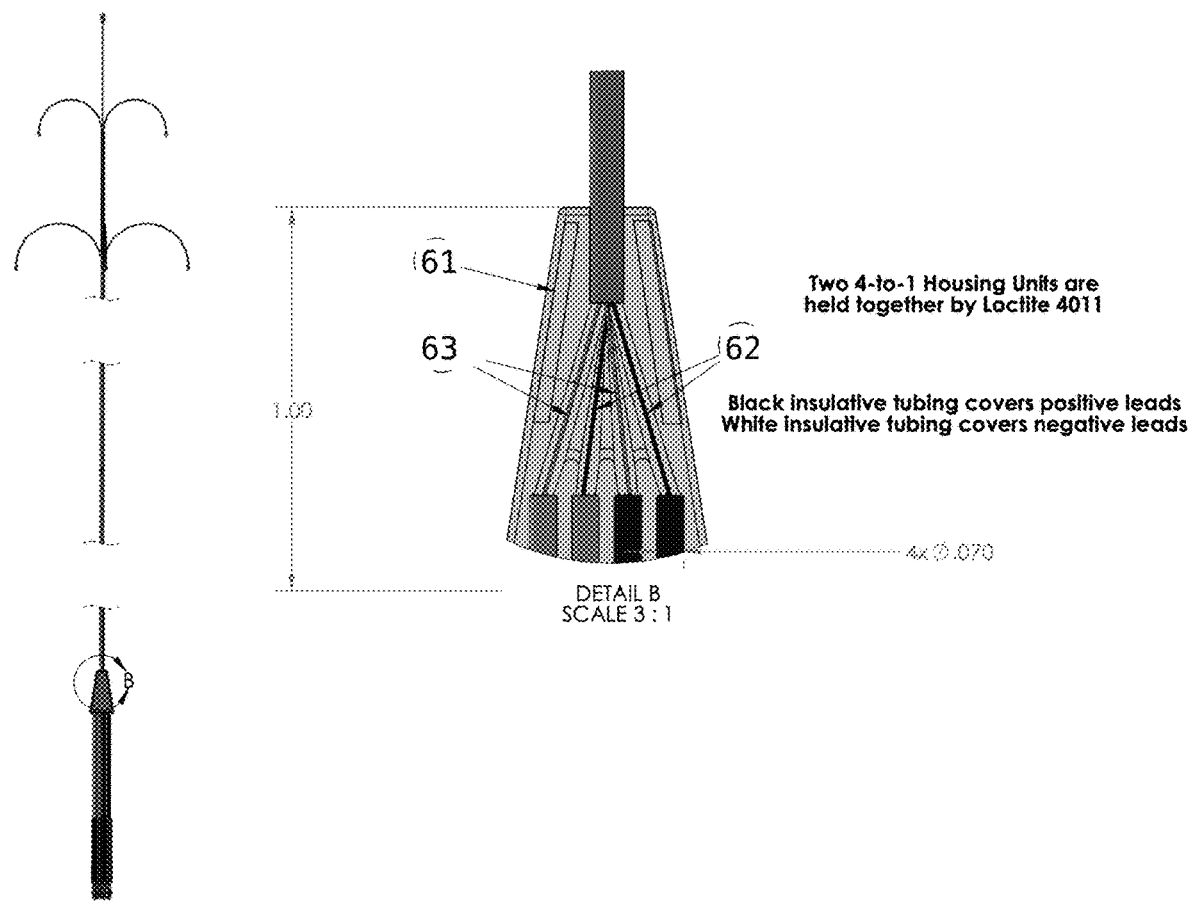
FIG. 6 is an illustration of one embodiment of the conical wire guide in relation to the proximal extrusion and the intracardiac portion of the device, according to the invention.

FIG. 6 is an illustration of one embodiment of the conical wire guide in relation to the proximal extrusion and the intracardiac portion of the device, according to the invention. FIG. 6 shows splitter housing unit 61 with atrial leads in channel 62, and ventricle leads in channel 63.

Figure 7:
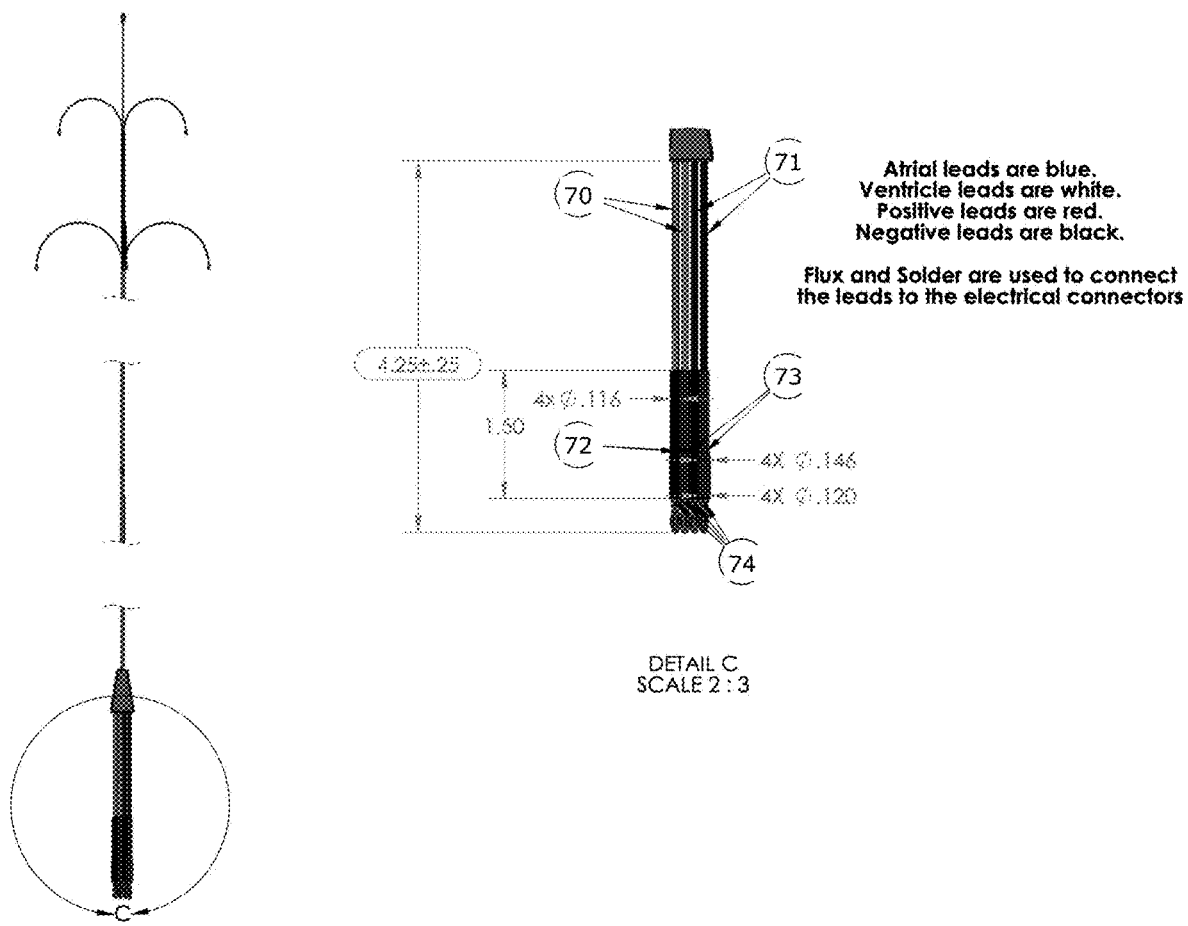
FIG. 7 is an illustration of one embodiment of the external lead terminal housing in relation to the proximal extrusion and the intracardiac portion of the device, according to the invention.

FIG. 7 is an illustration of one embodiment of the external lead terminal housing in relation to the proximal extrusion and the intracardiac portion of the device, according to the invention. FIG. 7 shows ventricle leads 70, atrial leads 71, negative leads 72, positive leads 73, and electrical connectors 74 to connect the leads to the electrical connection.

Figure 8:
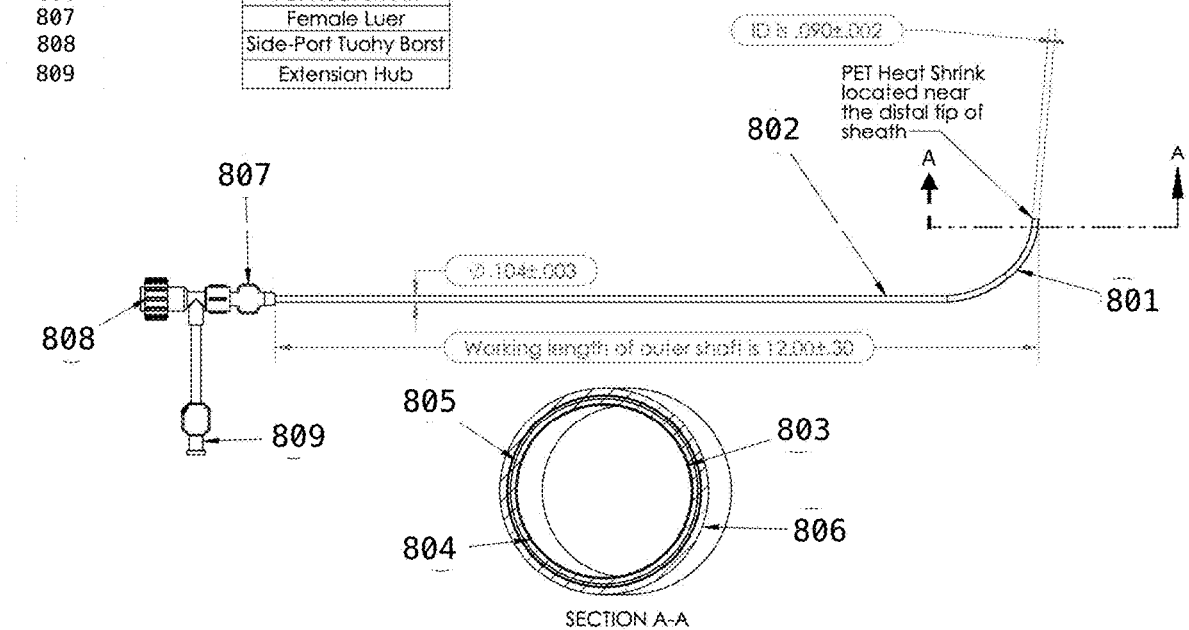
FIG. 8 is an illustration of one embodiment of the outer shaft with an extension hub, side-port Tuohy-Borst, female luer, and layered construction of the outer sheath, according to the invention.

FIG. 8 is an illustration of one embodiment of the outer shaft with an extension hub, side-port Tuohy-Borst, female luer, and layered construction of the outer sheath, according to the invention. FIG. 8 shows distal extrusion 801, proximal extrusion 802, PTFE liner 803, Tie layer 804, braid wire 805, PET heat shrink 806, female Luer 807, side-port Touhy-Borst 808, and extension hub 809.

Figure 9:
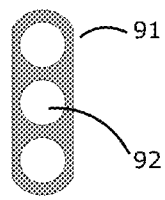
FIG. 9 is a cross-sectional illustration of the stoplight extrusion used for the ventricle leads.

FIG. 9 is a cross-sectional illustration of the stoplight extrusion 91 used for the ventricle leads. This figure shows the ventricular extrusion frame 91 having ventricle lead conduits (lumens) 92 for delivering the ventricle leads.

Figure 10:
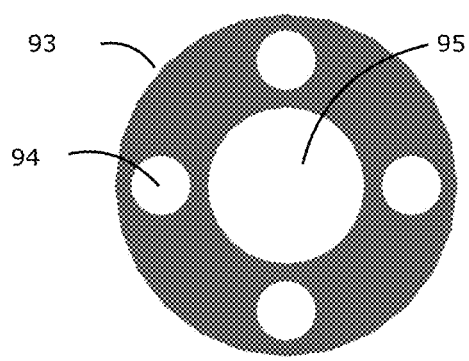
FIG. 10 is a cross-sectional illustration of the 4+1 extrusion used for the four atrial leads and the inner ventricular sheath.

FIG. 10 is a cross-sectional illustration of the 4+1 extrusion used for the four atrial leads and the inner ventricular sheath. This figures shows the atrial extrusion frame 93 having perimeter atrial lead conduits (lumens) 94 for delivering the atrium leads, and the central axial conduit (lumen) 95 for delivering the ventricular sheath to the ventricle.

Figure 11:
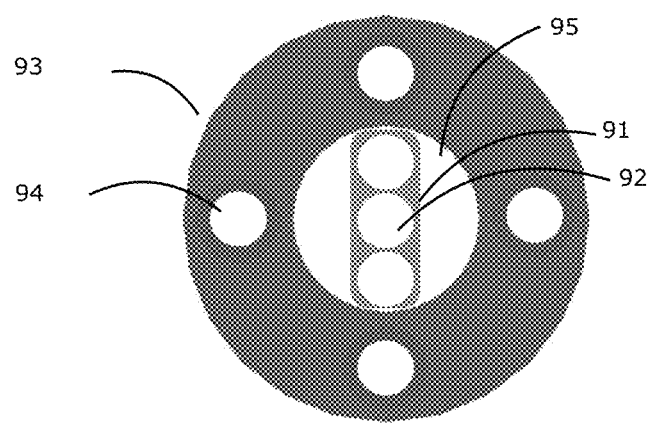
FIG. 11 is a cross-sectional illustration of the stoplight extrusion used for the ventricle leads disposed within the 4+1 extrusion used for the four atrial leads.

FIG. 11 is a cross-sectional illustration of the stoplight extrusion used for the ventricle leads disposed within the 4+1 extrusion used for the four atrial leads. This figure shows the ventricular sheath disposed within the central axial conduit (lumen) of the atrial sheath. The figure shows atrial extrusion frame 101 having atrium lead conduits (lumens) 102 for delivering the atrium leads, and shows ventricular extrusion frame 91 disposed within the central axial conduit (lumen) 103. The ventricular extrusion frame 91 is shown having ventricular lead conduits (lumens) 92 for delivering the atrium leads.

Figure 12:
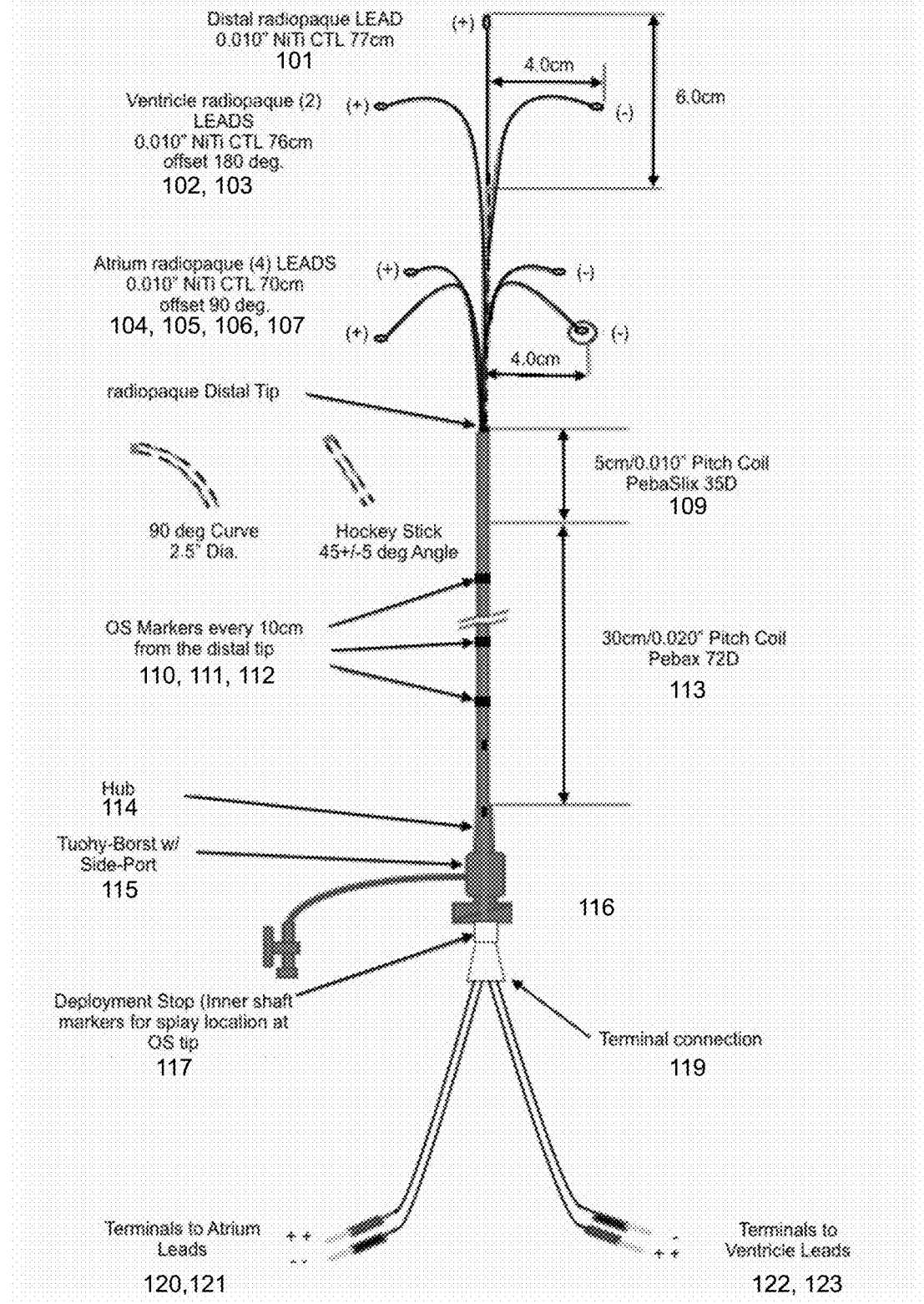
FIG. 12 is a schematic view of one embodiment of the device, illustrating the atrial leads, the ventricular leads, the retractable sheath, the combined hub and terminal connection, and steerable deployment mechanism, and the external lead terminals, according to the invention.

Referring now to FIG. 12 is a schematic view of one embodiment of the device, illustrating the atrial lead wires, the ventricular lead wires, the retractable sheath, the combined hub and terminal connection, and steerable deployment mechanism, and the external lead terminals, according to the invention. FIG. 12 shows a distal central radio-opaque lead wire 101 is shown as one of a three-part set of ventricle lead wires. Ventricle lead wires 102 and 103 are shown bent at 90 degrees away from the central axis of lead wire 101, and are shown in a 180 degrees opposition position from each other—lead 102 is 180 degrees opposite lead wire 103 in the y-axial plane.

In a preferred embodiment, ventricle leads are formed from 0.010" stainless steel or Nitinol. Lead wire 101 extends axially 6 cm from a distal radio-opaque band. Lead wires 102 and 103 bend away from the central lead and extend 4 cm away, each, from the central axis, respectively.

Atrium lead wires 104, 105, 106, 107 are bent 90 degrees extending away from the central axis, and are also bent 90 degrees from each other in the y-axis plane. Atrium leads extend 4 cm away, each, from the central axis, respectively.

Steerable catheter sheath is comprised of a distal portion 109 that is 5 cm in length and has a 0.010" pitch coil. In a preferred embodiment, the distal portion is made from PebaSlix 35D. Steerable catheter sheath is also comprised of a proximal portion 113 that is 30 cm in length and has a 0.020" pitch coil. In a preferred embodiment, the proximal portion is made from Pebax 72D. The sheath is configured to provide a 90 degree curve over a 2.5" diameter bend, and is also configured to provide a hockey-stick bend at a 45 degree angle+/−5 degrees. Sheath has OS markers 110, 111, 112 located every 10 cm along its length from the distal tip 108.

At a proximal end, sheath has a glued hub 114, a Touhy-Borst access connector with a side port 115. Actuator dial 116 is located at the proximal end of the sheath and allows the sheath to be shaped and controlled. Red deployment stop 117 connects the last 20 cm 118 of the sheath to the cable junction housing 119.

Programmable Leads

Atrium lead terminals 120, 121 and ventricle lead terminals 122, 123 allow the device to be connected to and operated from an external unit such as a ICD, pacer, diagnostic, or other unit that can provide sensor operation, stimulation signal, programming for individual leads to improve sensing, avoid over-sensing of the ventricular lead by T-waves or other noise or attenuating or interfering signals, avoid over-sensing of the atrium leads by the R-wave, avoid cross-talk, or customize sensing and stimulation on a lead-by-lead basis.

Also contemplated as within the scope of the invention is the use digital signal processing in conjunction with the use of multiple leads. Multiple input, multiple output (MIMO), single input multiple output (SIMO), single input single output (SISO), and multiple input single output (MISO) can be programmed in the control unit to take advantage of the multiple lead architecture. For example, decreasing sensitivity of certain leads and increasing sensitivity of other leads during a depolarization cycle (PQRST) allows the invention to increase SNR in the sensing function. Similarly, decreasing or increasing stimulatory signals to one or more leads allows the invention to more accurately provide stimulation to the atrial endothelium and the ventricular endothelium, which may optionally include other cardiac tissue to provide a level of granularity to the stimulation function not previously available to practitioners. Likewise, unlike previous devices, the availability of multiple, programmable leads means that sensing leads are not required to share the function of a shocking/stimulation leads. Further, damaged or degraded leads can be bypassed allowing continued functioning without requiring the entire device to be removed from a patient, this increasing the longevity of implanted devices using the inventive technology.

As is customary with implantable pulse generators, the device may be programmable to achieve either conventional bipolar or unipolar stimulation or to achieve the stimulation of the present invention through an external programmer or controlled automatically by the device. The selection can be based on user preference or be driven by physiological factors such as widths of the patient's QRS complex or the conduction interval between the stimulus to a far away region in the heart. In addition switching between the pacing of the present invention and conventional pacing can also be determined by the percentage of pacing with a preference for a higher percentage with the pacing of the present invention. Further, the switching from the conventional pacing to the present invention pacing can be used when there exists an exit block or the pacing electrode is located in infracted myocardium when conventional pacing can not effect the depolarization of the myocardium at the high output level. The automatic determination can be effected through the deployment of any automatic capture detection technology that exists in the prior art. Additionally, wireless network enabled switching function for therapy optimization can also be implemented with the present invention. In such case, certain patient physiologic data are gathered by the implantable device and sent to a remote server/monitor through a wireless communication network.

Figure 13:
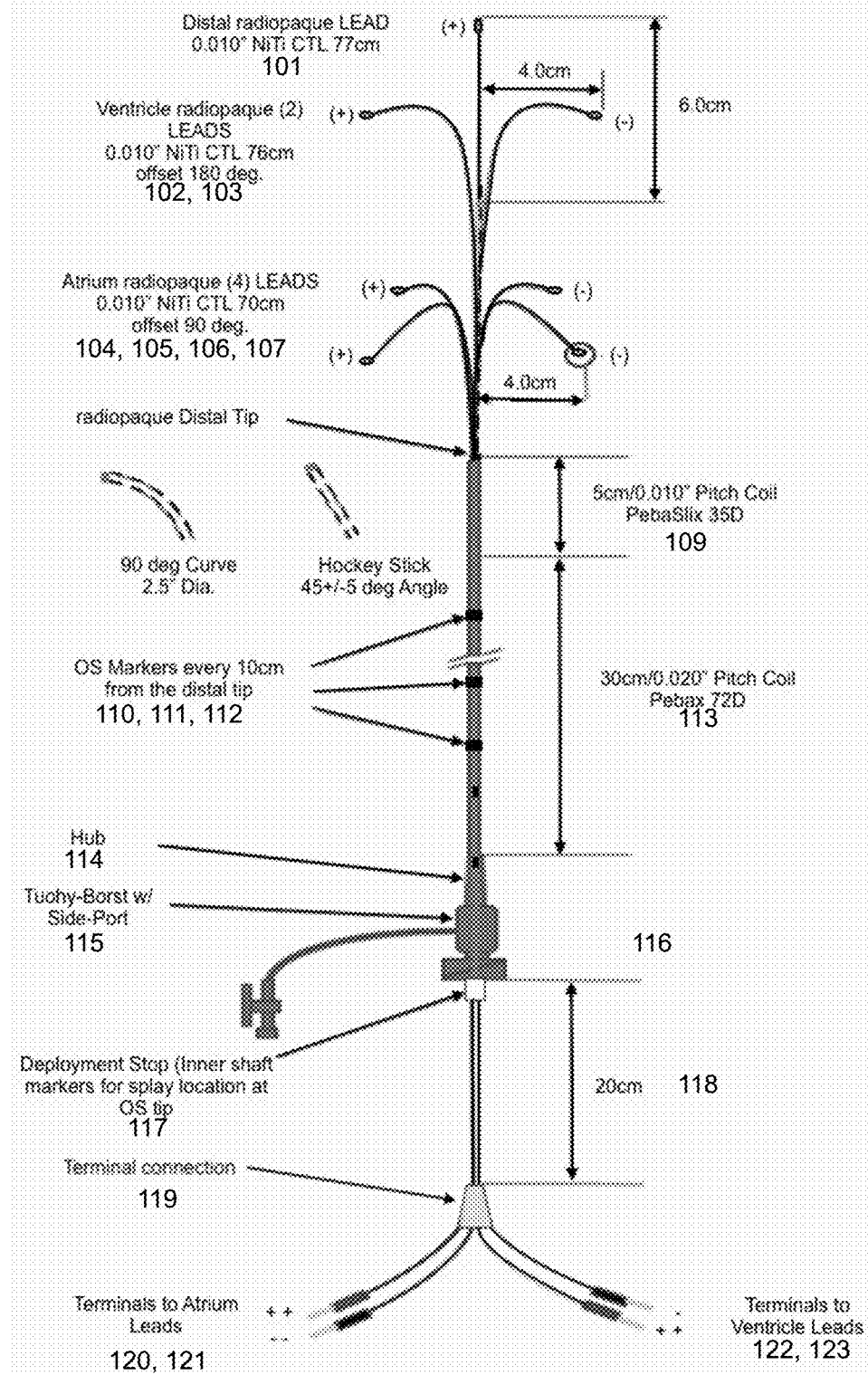
FIG. 13 is a schematic view another embodiment of the device, illustrating the atrial leads, the ventricular leads, the retractable sheath, the hub, the independent terminal connection, and steerable deployment mechanism, and the external lead terminals, according to the invention.

FIG. 13 is a schematic view another embodiment of the device, illustrating the atrial leads 104, 105, 106, 107, the ventricular leads 101, 102, 103, the retractable sheath 109, 113, the hub 114, the independent terminal connection 119, and steerable deployment mechanism 116, and the external lead terminals 120, 121, 122, 123, according to the invention. This figure also shows a 20 cm segment 118 from the deployment stop 117 and the terminal connection 119.

Figure 14:
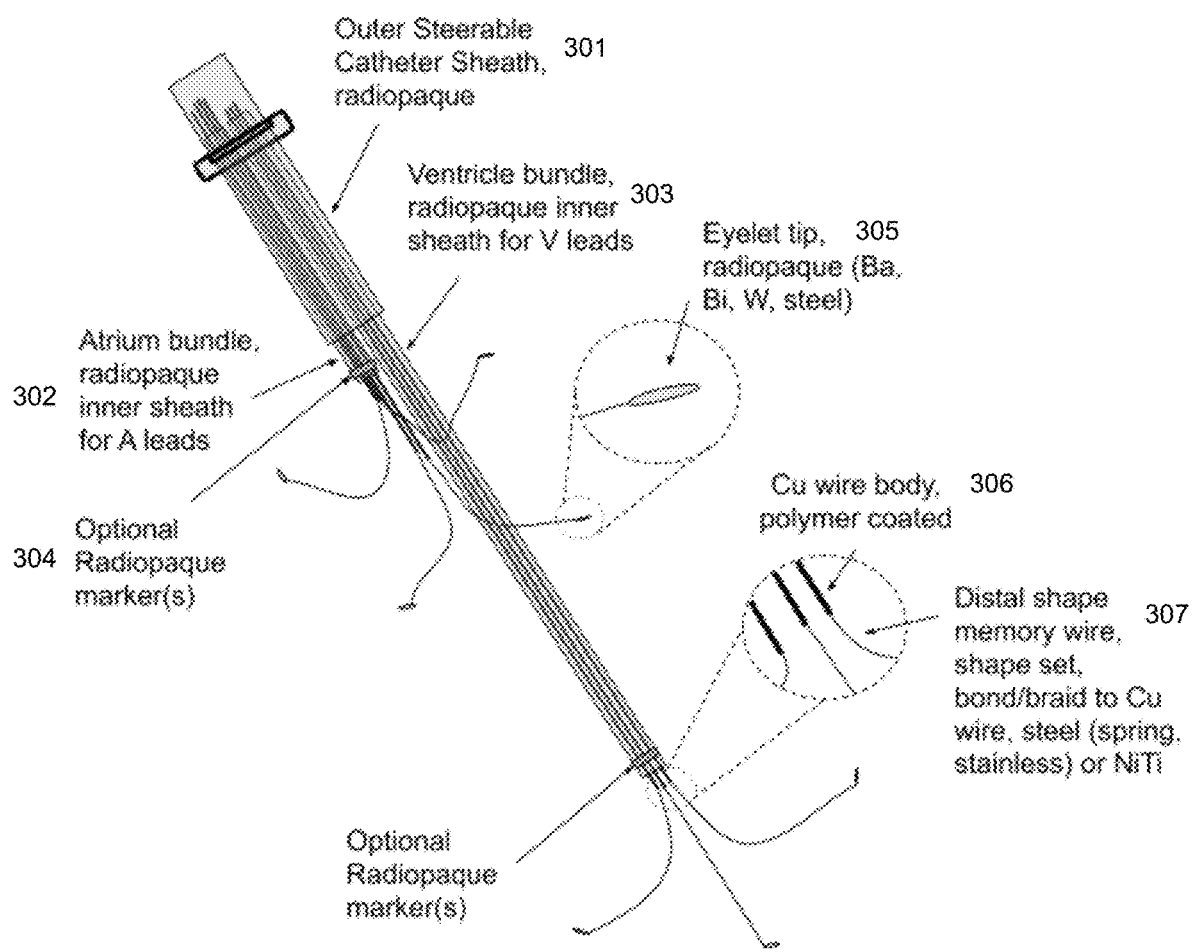
FIG. 14 is a schematic of the two-inner sheath (dual lumen) embodiment illustrating the outer steerable catheter sheath housing the two inner sheaths, with one inner sheath having the ventricle leads and the other inner sheath having the atrium leads, according to the invention.

FIG. 14 is a schematic of the two-inner sheath embodiment illustrating the outer steerable catheter sheath 301 housing the two inner sheaths 302, 303, with one inner sheath 303 having the ventricle leads and the other inner sheath 302 having the atrium leads, according to the invention. Eyelet tip 305 is constructed with radiopaque material and configured/shaped, e.g. as a loop, to have a surface area larger than the point cross-section of a wire lead. In a preferred embodiment, the eyelet tip is 0.2-1.0 mm in area. Copper wire body portion 306 of the wire lead runs the length of the catheter from the pacemaker up to the distal shape memory portion 307. Shape memory portion 307 is attached to the copper wire 306 by bond, braid, weld, etc.

Figure 15:
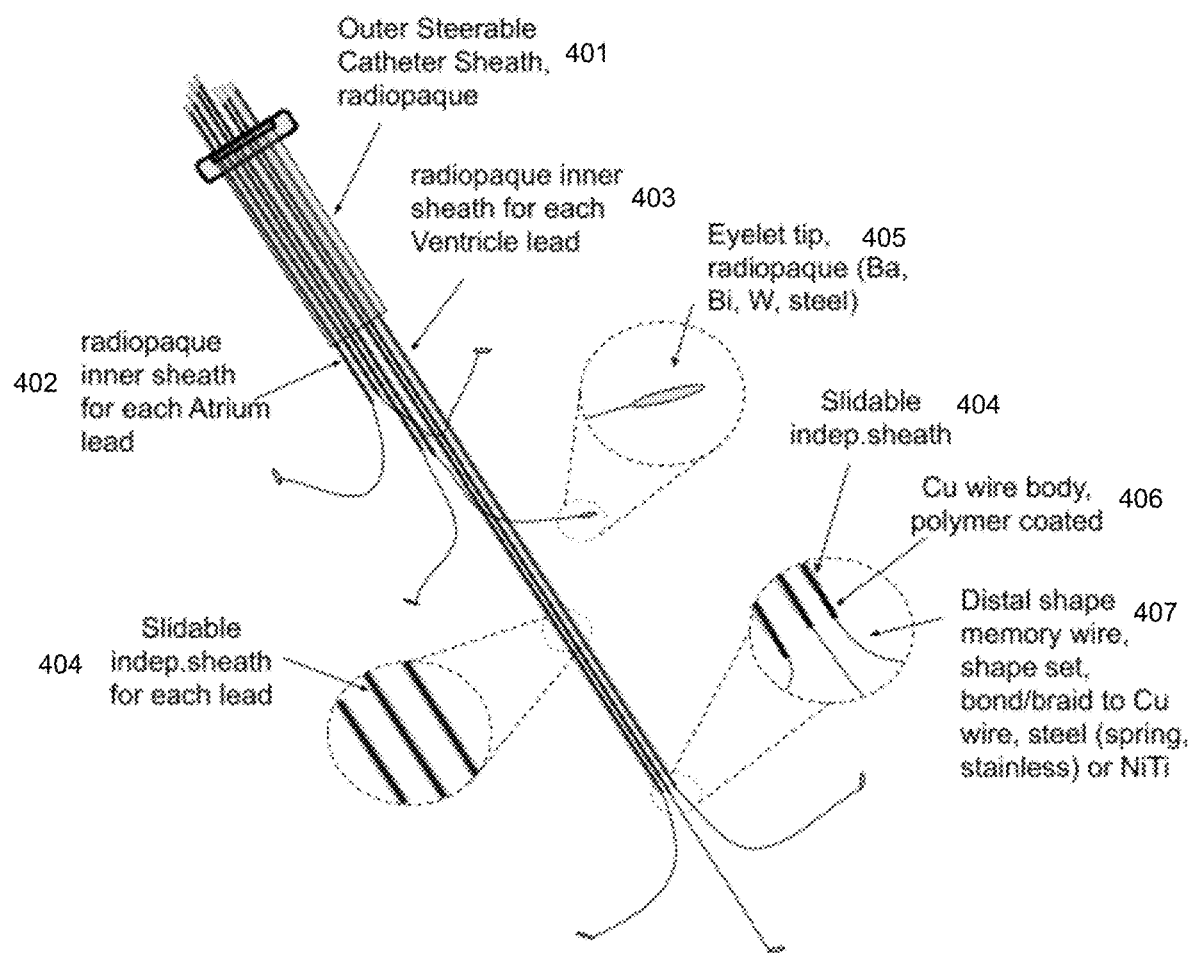
FIG. 15 is a schematic of the seven-inner sheath (multi-lumen) embodiment illustrating the outer steerable catheter sheath housing the seven inner sheaths, with each inner sheath its own lead, and providing three (3) ventricle leads and four (4) atrium leads, according to the invention.

FIG. 15 is a schematic of the seven-inner sheath (multi-lumen) embodiment illustrating the outer steerable catheter sheath 401 housing the seven inner sheaths, with each inner sheath 404 having its own lead, and providing three (3)

ventricle leads 403 and four (4) atrium leads 402, according to the invention. Eyelet tip 405 is constructed with radiopaque material and configured/shaped, e.g. as a loop, to have a surface area larger than the point cross-section of a wire lead. In a preferred embodiment, the eyelet tip is 0.2-1.0 mm in area. Copper wire body portion 406 of the wire lead runs the length of the catheter from the pacemaker up to the distal shape memory portion 407. Shape memory portion 407 is attached to the copper wire 406 by bond, braid, weld, etc.

Figure 16:
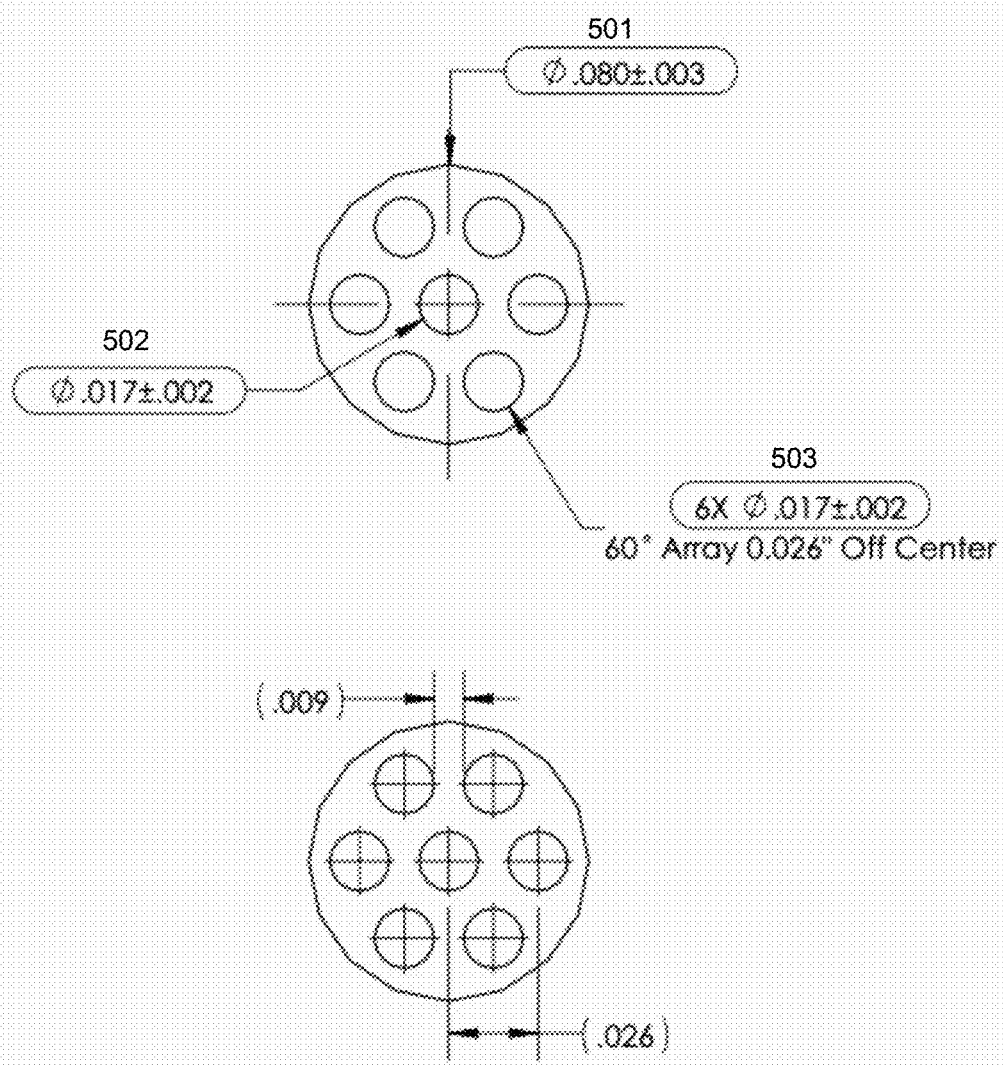
FIG. 16 is a schematic of a cross-section of the seven-inner sheath (multi-lumen) embodiment illustrating the outer steerable catheter sheath housing the seven inner sheaths, with each inner sheath its own lead, and providing three (3) ventricle leads and four (4) atrium leads, according to the invention.

FIG. 16 is a schematic of a cross-section of the seven-inner sheath (multi-lumen) embodiment 501 illustrating the outer steerable catheter sheath 501 housing the seven inner sheaths 502, 503, with each inner sheath its own lead, and providing three (3) ventricle leads and four (4) atrium leads, according to the invention.

Figure 17:
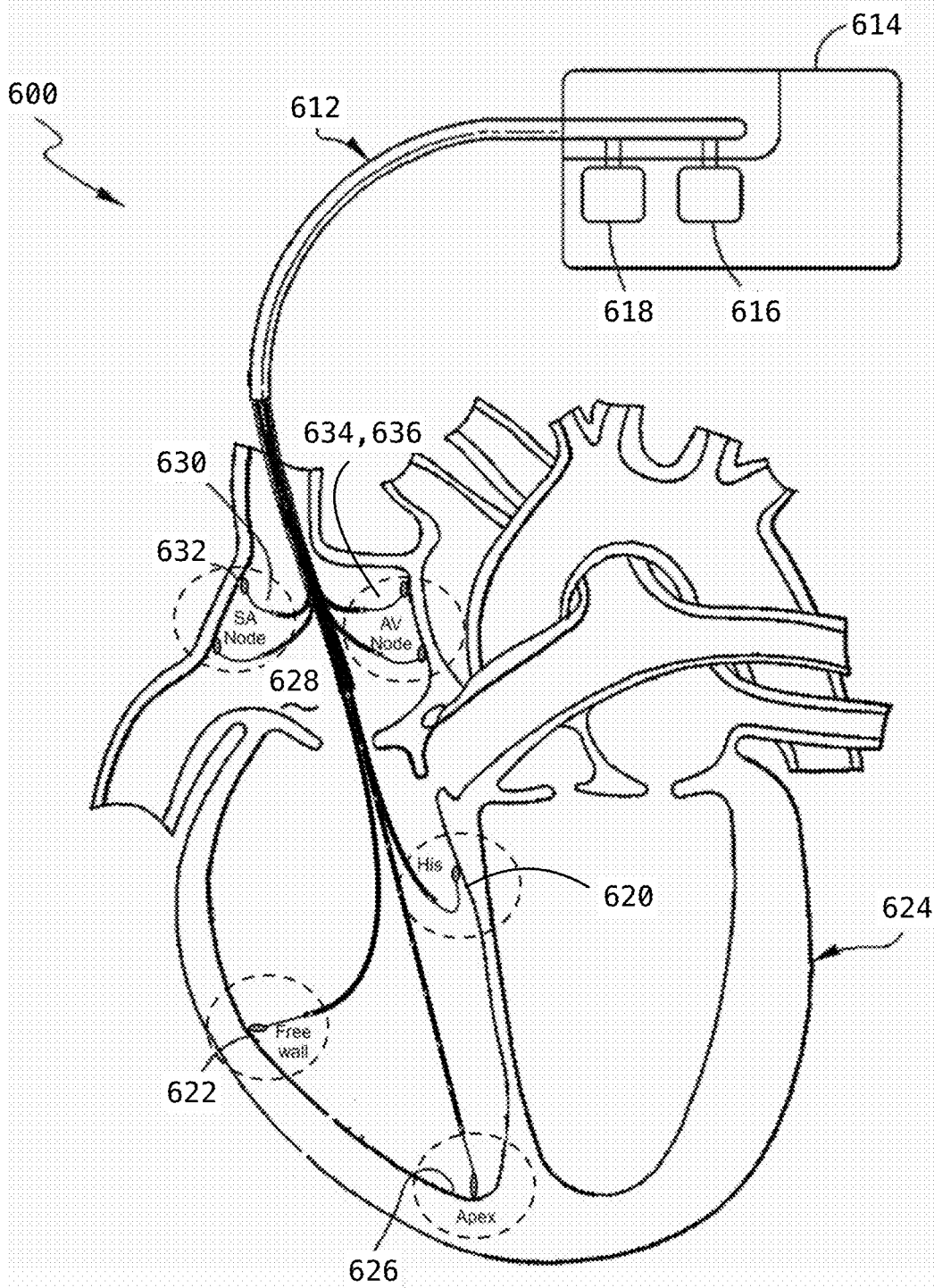
FIG. 17 is a schematic view of a cross-section of a human heart, a plurality of electrodes inserted in the ventricle and atrium contacting the walls of the heart chambers and a pacer, according to the invention.

Referring now to the FIG. 17, an external pacemaker 614 is shown connected to a bundle of insulated wire electrical conductors wrapped in a sheath 612. Specifically, the pacemaker 614 as shown is connected to a bundle of seven insulated conductive wires, three wires 620, 622, 626 of which are disposed within the ventricle and four wires 630, 632, 634, 636 of which are disposed in the atrium 628. The wires are bundled in a sheath 612 that was inserted into the ventricle and then pulled backward, exposing the three ventricle leads which are now contacting the walls of the ventricle due to the retained curved memory of each wire. As the sheath 612 is further withdrawn into the atrium, four additional electrodes 630, 632, 634, 636 are shown contacting atrial chamber 628 walls in accordance with the present invention.

As shown in the drawing, the invention as disclosed is a low profile transvenous electrode system for sequentially pacing both the atrium and ventricle of the heart in a dual chamber mode. As shown in the drawing, there are a plurality of insulated electrical wires represented that are electrical conductors and that are wrapped in electrical insulators. The wires are bundled together into two separate in-line sets of leads. Each wire has memory and is resilient. During manufacturing, each wire is pre-formed in a particular curvature and length so that when disposed within a heart chamber, atrium or ventricle, the electrode end of the wire will engage the chamber wall for electrical pulse transfer. In a preferred embodiment, the device comprises three (3) ventricular leads and four (4) atrial leads, made from shape memory material. Two of the three ventricular leads are bent at 90 degrees from the central axial lead and are 180 degrees from each other. The four atrial leads are bent at 90 degrees from the central axis (x-axis), and are each separated 90 degrees from the adjacent leads, in the y-axis plane.

Both sets of leads may also be mounted and contained inside a slender e.g. 8 Fr (8/3=2.66 mm), tubular, flexible elongated e.g. 35 cm retaining sheath that serves as a guide and delivery system during insertion and removal of the electrode system.

Each of the wires in the ventricle could be of different lengths with different shapes so that when the sheath is removed, each wire expands out by memory to have sufficient resiliency in distance to contact the inner wall of the ventricle as shown with the electrode points flush against the ventricle wall. There is a certain amount of resiliency in each wire holding the wire against the wall during pacing in the position as shown. The four wires used in the atrium are also pre-formed in curvature and length so that when the sheath is removed, wires expand resiliently against the walls of the atrium as shown in the drawing with electrode points disposed at the end of each wire against the wall tissue. The resiliency in each wire will hold the electrodes against the wall of the atrium while pacing.

The external pacemaker 14 provides the electrical pulses for the sequential pacing. The pacemaker 14 has two sequential pulse generators 16 and 18 which are connected to the proximal ends of the wires for providing the sequential pulses to both the ventricle through wires and to the atrium through wires. The external pacemaker itself is conventional in operation.

Pulse Generator

The term "pulse generator" is intended to include pacemakers and cardia resynchronization therapies (CRT), all known in the art.

It will be appreciated that the prior art contains numerous examples of cardiac leads for placement in a chamber of the heart, electrodes, attachment mechanisms, conductors and/or connector pins.

The pulse generator contains internal circuitry for creating electrical impulses which are applied to the electrodes after the lead is connected to the pulse generator. Also, such circuitry may include sensing and amplification circuitry so that electrodes may be used as sensing electrodes to sense and report on the patient's electrophysiology.

The lead may be introduced to the vasculature through a small incision and advanced through the vasculature and into the right atrium RA and right ventricle to the position. Such advancement typically occurs in an electrophysiology lab where the advancement of the lead can be visualized through fluoroscopy.

The pulse generator may contain a battery as a power supply.

The pulse generator circuitry controls the parameters of the signals coupled to the electrodes. These parameters can include pulse amplitude, timing, pulse duration by way of example. The internal circuitry further includes circuit logic permitting reprogramming of the pulse generator to permit a physician to alter pacing parameters to suit the need of a particular patient. Such programming can be affected by inputting programming instructions to the pulse generator via wireless transmission from an external programmer. Most commonly, the electrode is connected by the circuitry to an electrical ground.

In a preferred embodiment, the pulse generator may be external and coupled to the electrodes by percutaneous leads or wireless transmission.

Electrode Leads

The leads which are the wire conductors and electrodes are manufactured in different lengths and curved resiliently as discussed above with approximate distances between the electrodes to create a configuration or pattern as shown.

In a preferred embodiment, the leads are established inside the ventricle and established in the atrium.

The wires may have memory and with their pre-formed curvatures are resilient enough to be bundled in a small sheath prior to being mounted within the heart chambers. Both sets of wires may be contained inside a single, cylindrical, flexible retaining sheath that is the guide and delivery system during insertion and removal of the electrode system.

The ventricular electrodes may be pacemaker sensors or stimulators are released first after the retaining sheath has been successfully inserted into the right ventricle. The sheath may be retracted allowing the electrodes and wires to spread out and contact the endocardial surfaces. The wires expand outwardly as the sheath is removed engaging the tissue and chamber wall of the ventricle.

With a parallel configuration of wires is chosen, the wires can be released and make contact on the same plane within the ventricular chamber or they can be staggered.

The continued retraction of sheath may allow the escape of the atrial wires from the sheath which proceed toward the atrial tissue for engagement of the electrodes against the atrial wall.

Once the electrodes are disposed within the ventricular chamber and the atrium, sequential pacing can be initiated in the atrium and ventricle in a dual chamber mode providing an emergency pacemaker that will pace and sense both atrial and ventricular chambers and provide dual chamber control of the heart.

The dual chamber pacing refers to continuous monitoring of the spontaneous activity of the heart both in the atrial and in the ventricles interpreting the detective events according to certain accepted algorithms and providing stimuli to the chambers as needed to maintain a physiologically appropriate rhythm.

FIG. 18 is a chart of an acute first in human study and is useful to support an embodiment of the present invention. This figure shows an example study of a sample of 10 patients, although not necessarily for any specific indication. This figure illustrates that the device is positioned and deployed in the right side chambers of the heart with fluoroscopy guidance and once vascular access, internal jugular or subclavian is obtained. After deployment, catheterization and testing takes about 24 minutes to perform a diagnostic left heart catheterization and test the device as described, including to position and deploy the device, pace the RV, pace the A, synchronic AV pacing, perform a left side diagnostic, and then pace the RV, pace the A, synchronic AV pacing, and remove the device, according to the invention.

FIG. 19 is an example of a chart of data in an embodiment of the invention from a procedure recording a non-limiting preferred embodiment. This figure shows by subject and lead, the impedance, the threshold, and the current, recorded. This shows safe delivery with and without fluoroscopic guidance, successful pacing, excellent contact and hold of the leads against the cardiac tissue, with no adverse events or significant adverse events at discharge.

Figure 20A:
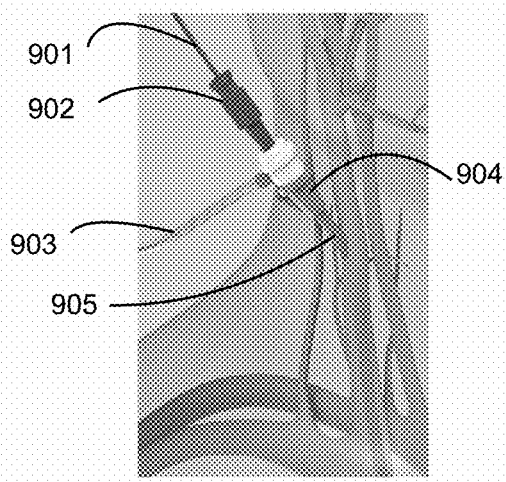
FIG. 20 is an illustration of one embodiment of a device being introduced into the jugular vein of a patient, with removal of the guidewire, and introduction of the transvenous dual-chamber sequential pacing device into the steerable catheter sheath, according to the invention.
Figure 20B:
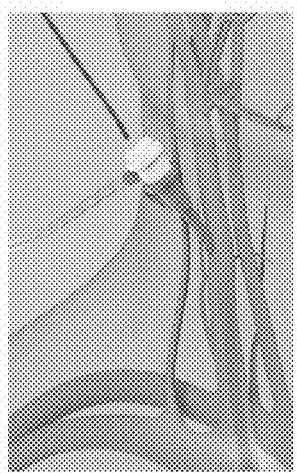
Figure 20C:
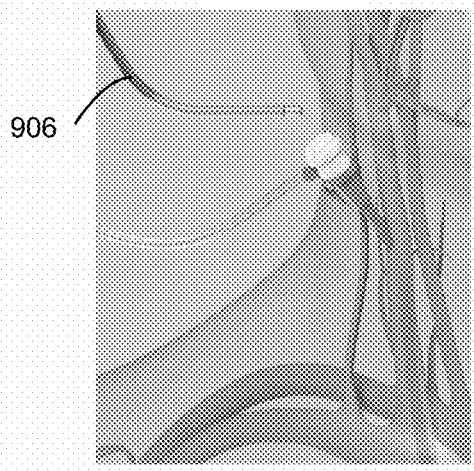

FIGS. 20A, 20B, 20C is a sequence illustration of one embodiment. FIG. 20A shows a device being introduced into the jugular vein of a patient using a guidewire 901 and introducer 902. Luer 903 is shown connecting near hub 904, with outer delivery catheter 905 accessing down the jugular vein. FIG. 20B shows removal of the guidewire 901. FIG. 20C shows introduction of the transvenous dual-chamber sequential pacing device having steerable catheter sheath 906 into the deliver catheter 905.

Figure 21:
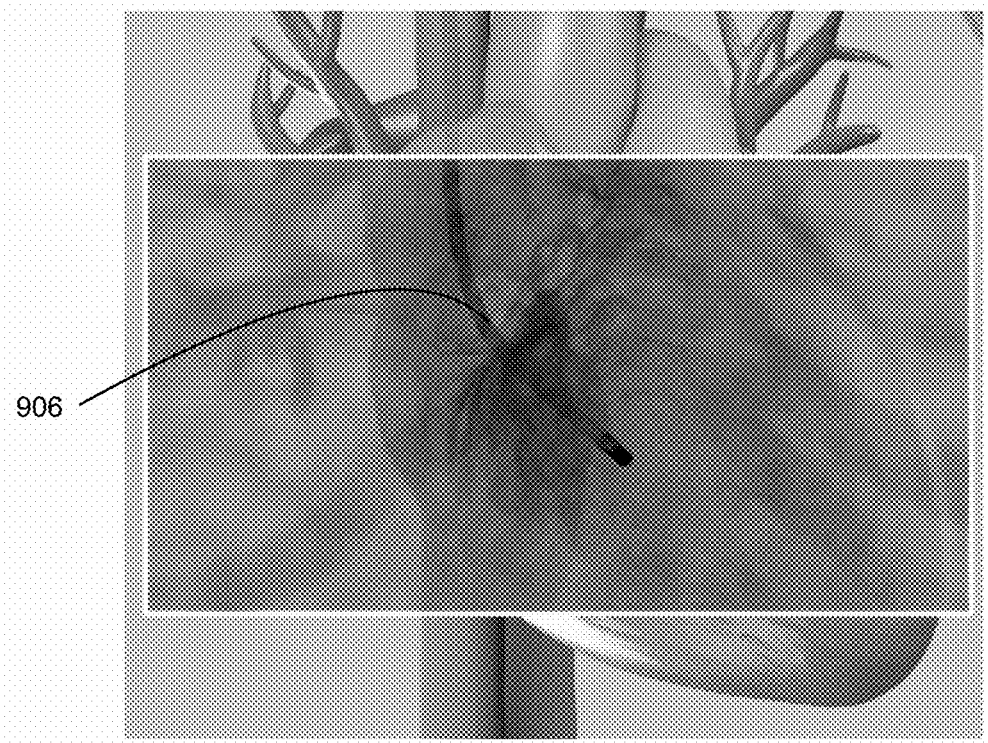
FIG. 21 is an illustration of one embodiment of the transvenous dual-chamber sequential pacing device deployed into a heart, as shown on fluoroscopic imaging, according to the invention.

FIG. 21 is an illustration of one embodiment of the transvenous dual-chamber sequential pacing device deployed into a heart using steerable catheter 906, as shown on fluoroscopic imaging.

Figure 22:
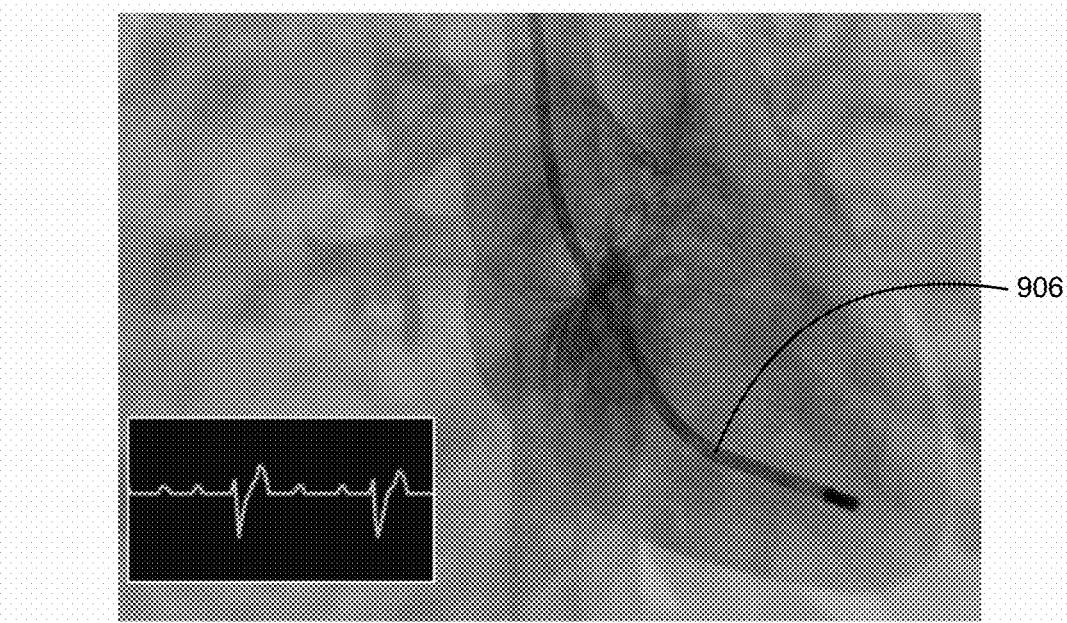
FIG. 22 is an illustration of one embodiment of the transvenous dual-chamber sequential pacing device deployed into a heart, as shown on fluoroscopic imaging, according to the invention.

FIG. 22 is an illustration of one embodiment of the transvenous dual-chamber sequential pacing device deployed into a heart using steerable catheter 906, as shown on fluoroscopic imaging.

Figure 23:
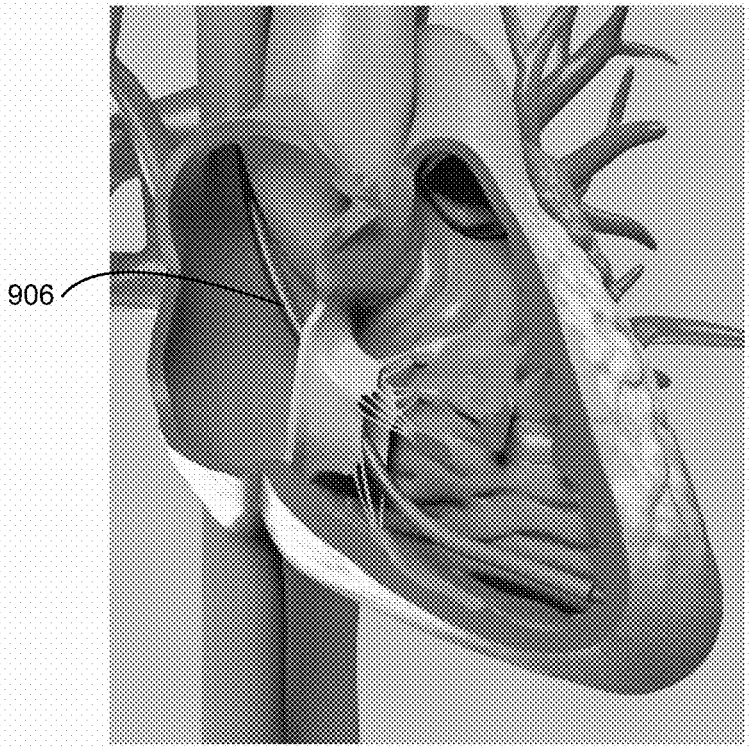
FIG. 23 is an illustration of one embodiment of the transvenous dual-chamber sequential pacing device deployed into a heart, as shown in a cut-away view into the heart, according to the invention.

FIG. 23 is an illustration of one embodiment of the transvenous dual-chamber sequential pacing device deployed into a heart using a steerable catheter 906, as shown in a cut-away view into the heart.

Figure 24:
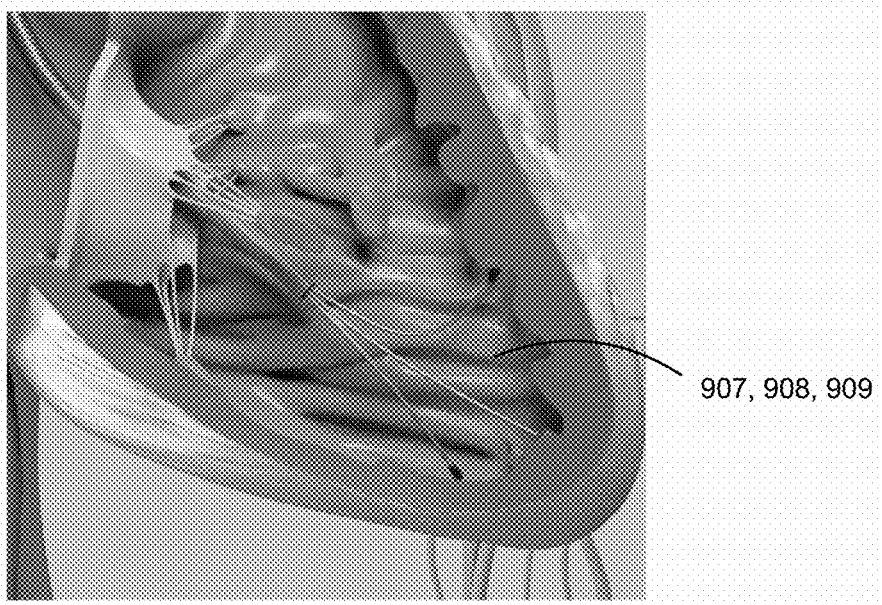
FIG. 24 is an illustration of one embodiment of the transvenous dual-chamber sequential pacing device deployed into a heart, with ventricle leads deployed from a movable inner sheath into the ventricle, according to the invention.

FIG. 24 is an illustration of one embodiment of the transvenous dual-chamber sequential pacing device deployed into a heart, with ventricle leads 907, 908, 909 deployed from a movable inner sheath into the ventricle.

Figure 25:
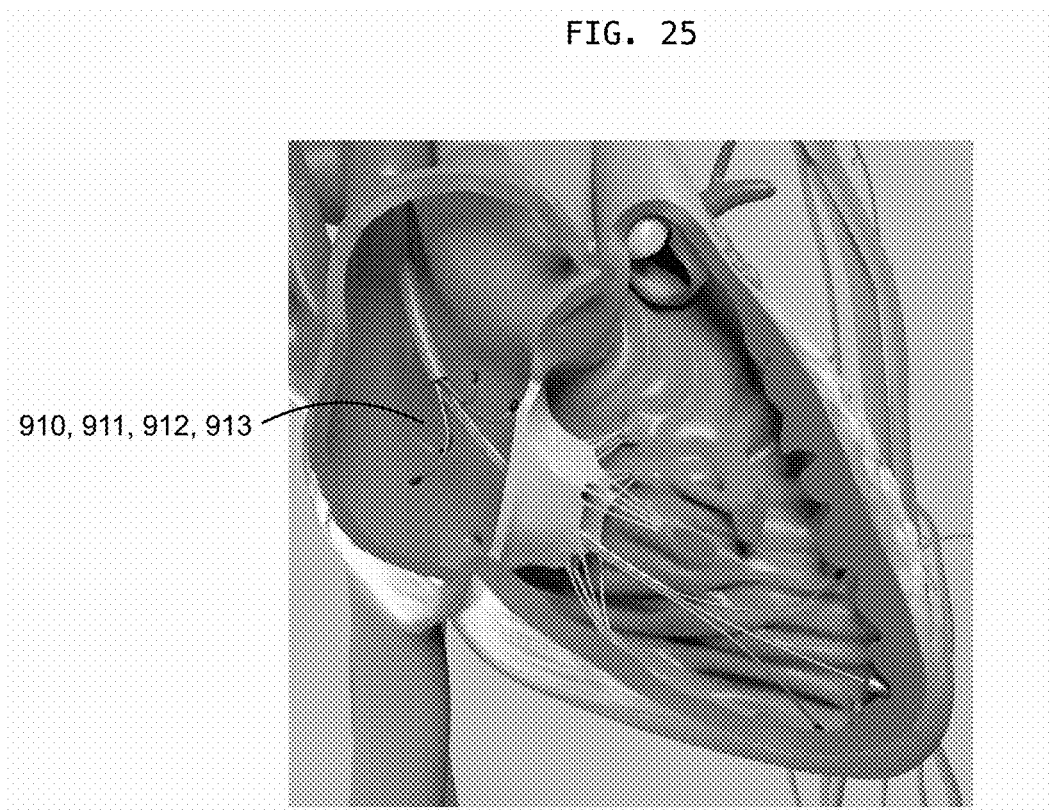
FIG. 25 is an illustration of one embodiment of the transvenous dual-chamber sequential pacing device deployed into a heart, with atrium leads being deployed from a movable inner sheath into the atrium, while ventricle leads have already been deployed into the ventricle, according to the invention.

FIG. 25 is an illustration of one embodiment of the transvenous dual-chamber sequential pacing device deployed into a heart, with atrium leads 910, 911, 912, 913 being deployed from a movable inner sheath into the atrium, while ventricle leads have already been deployed into the ventricle.

Figure 26:
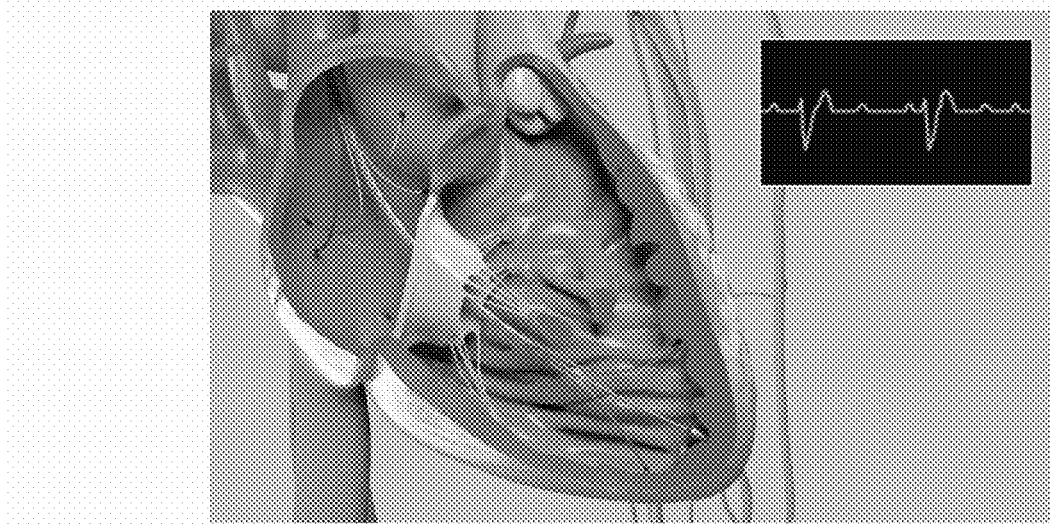
FIG. 26 is an illustration showing how the device can sense abnormal heart rhythm using the transvenous dual-chamber sequential pacing device deployed into a heart, according to the invention.

FIG. 26 is an illustration showing how the device can sense abnormal heart rhythm using the transvenous dual-chamber sequential pacing device deployed into a heart.

Figure 27:
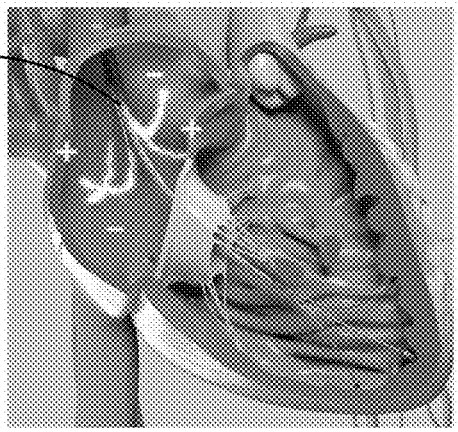
FIG. 27 is an illustration showing how the device can provide electrical stimulation to the atrium using the transvenous dual-chamber sequential pacing device deployed into a heart, according to the invention.

FIG. 27 is an illustration showing how the device can provide electrical stimulation to the atrium using the transvenous dual-chamber sequential pacing device deployed into a heart. FIG. 27 shows atrium leads 910-911-912-913 providing stimulation to the atrium.

Figure 28:
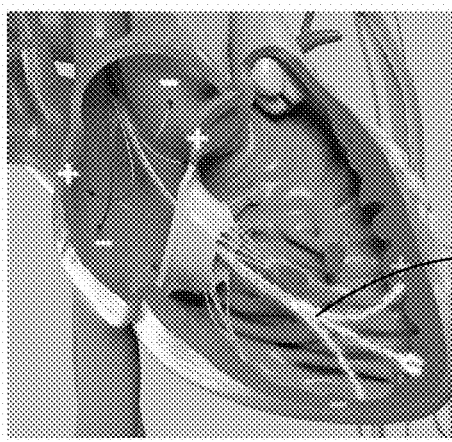
FIG. 28 is an illustration showing how the device can provide electrical stimulation to the ventricle using the transvenous dual-chamber sequential pacing device deployed into a heart, according to the invention.

FIG. 28 is an illustration showing how the device can provide electrical stimulation to the ventricle using the transvenous dual-chamber sequential pacing device deployed into a heart. FIG. 28 shows ventricle leads 907-908-909 providing stimulation to the ventricle.

Figure 29:
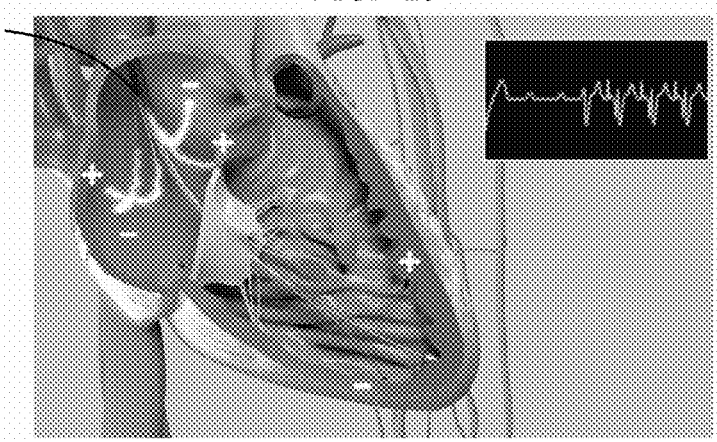
FIG. 29 is an illustration showing how the device can sense the corrected normal heart rhythm using the transvenous dual-chamber sequential pacing device deployed into a heart, according to the invention.

FIG. 29 is an illustration showing how the device can sense the corrected normal heart rhythm using the transvenous dual-chamber sequential pacing device deployed into a heart. FIG. 29 shows atrium leads 910-911-912-913 again providing stimulation to the atrium.

Figure 30:
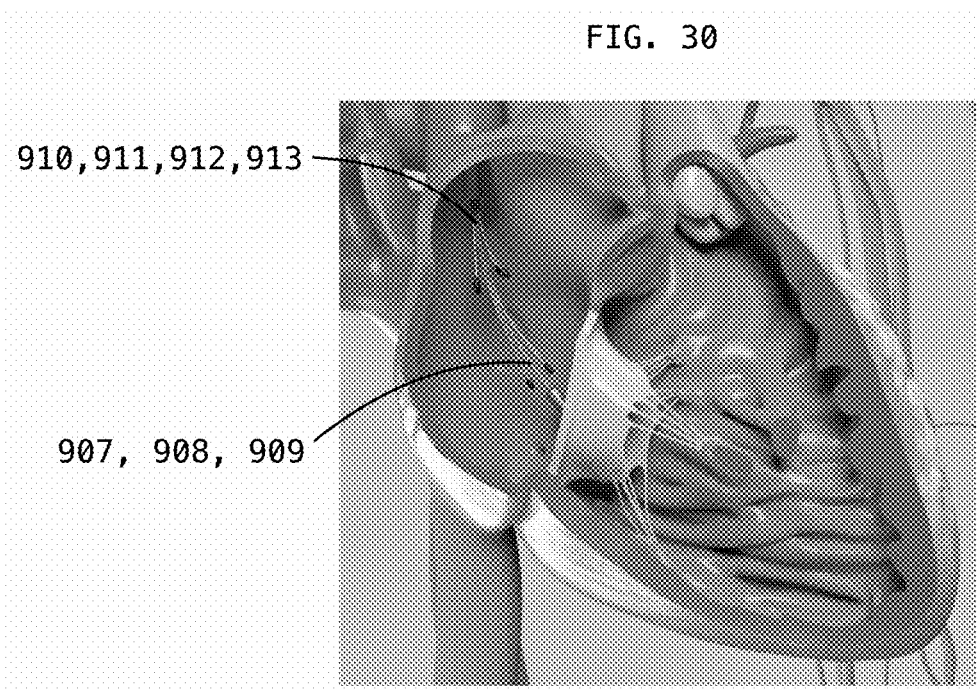
FIG. 30 is an illustration showing how the device is removed after being deployed into a heart, according to the invention.

FIG. 30 is an illustration showing how the device is removed after being deployed into a heart. Here, the leads may be removed by simply pulling, in one embodiment. In another embodiment, the sheath(s) may be re-introduced to gather the leads prior to removal. FIG. 30 shows atrium leads 910-911-912-913 and ventricle leads 907-908-909 exiting the heart.

Figure 31:
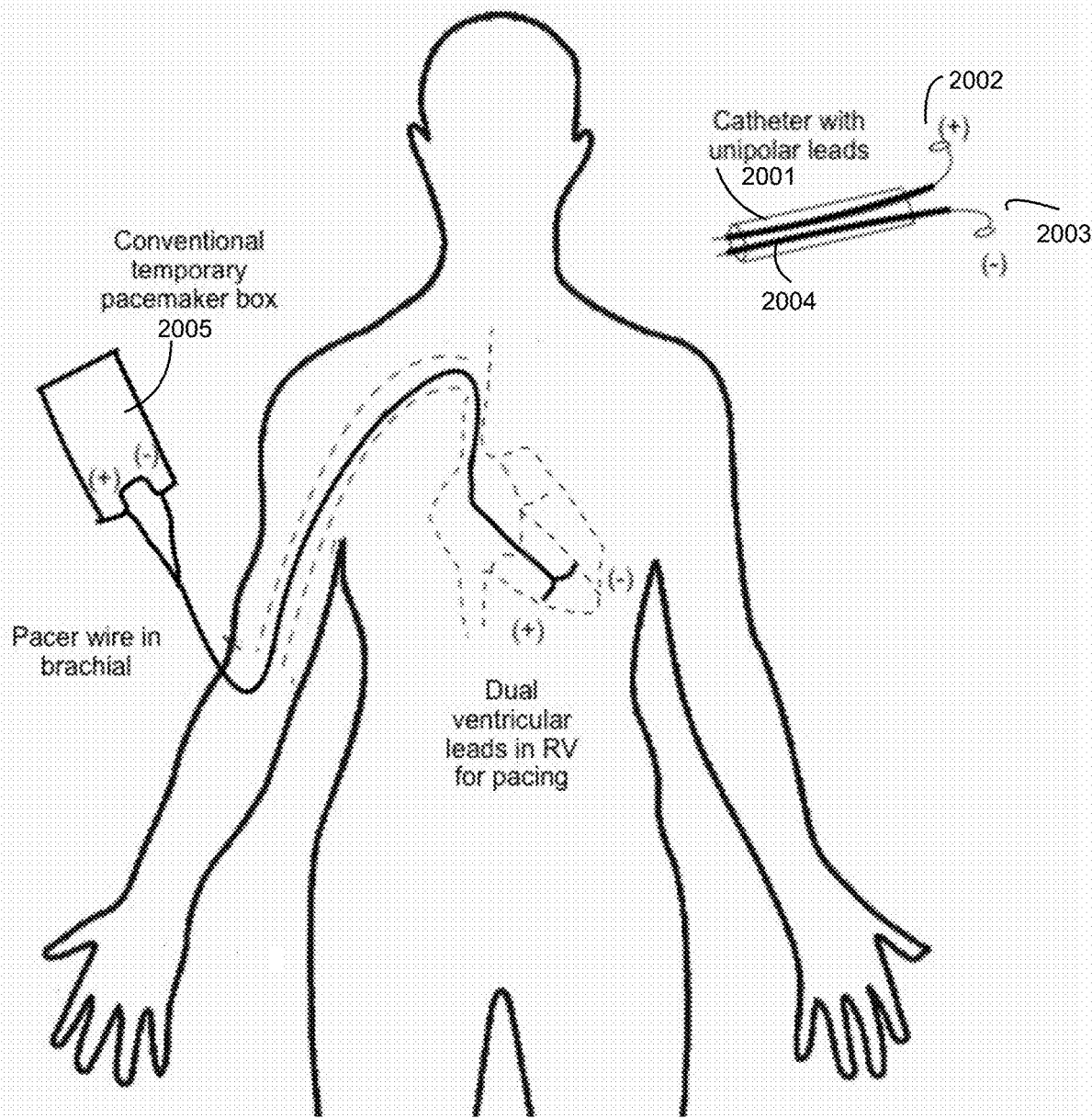
FIG. 31 is an illustration of a ventricle only embodiment of the invention.

FIG. 31 is an illustration of a ventricle only embodiment of the invention. This figure shows catheter 2001 having the unipolar leads 2002, 2003 disposed therein. The leads 2002, 2003 are shown having optional radiopaque insulating covering 2004 in a non-limiting embodiment. Conventional temporary pacemaker 2005 is attached to the leads by way of the brachial vein to provide dual ventricular leads in the right ventricle for pacing. In a non-limiting preferred embodiment, the catheter if 4 French in size, or 4/3 mm (1.33 mm) in diameter. Leads 2002, 2003 may include radiopaque eyelet tips, and may also include a proximal portion made of copper with a distal portion made from steel or nickel-titanium (NiTi) alloy, in a non-limiting embodiment as previously described.

Figure 32:
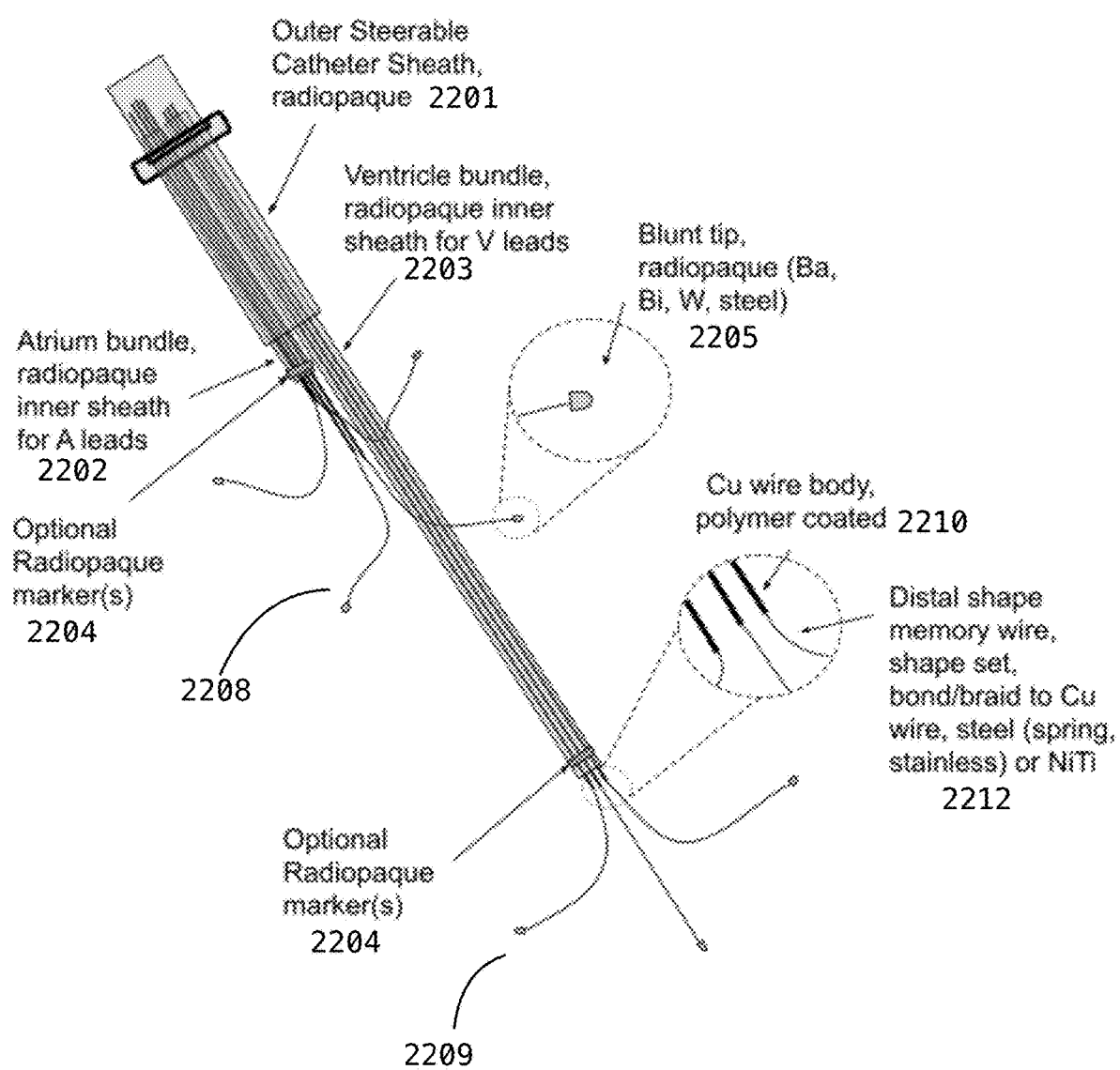
FIG. 32 is an illustration of leads having a shape and constructed of materials to reduce endothelial injury and maximize energy transfer and signal transduction.

FIG. 32 is an illustration of leads having a shape and constructed of materials to reduce endothelial injury and maximize energy transfer and signal transduction. This figure shows the atrium leads and the ventricle leads having a blunt electrode tip 2105. The blunt, non-damaging tip 2105 may include radio-opaque materials or coatings. Non-limiting materials may be selected from barium, bismuth, tungsten, steel, or other known RO materials. FIG. 31 also shows outer sheath 2101 having the atrium inner sheath 2102 and the ventricle inner sheath 2103 disposed therein. Atrium leads 2108 and ventricle leads 2109 are shown extending from their respective inner sheaths. Optional radio-opaque markers 2104 may also be mounted at various locations to assist the endoscopic practitioner with visualizing the proper placement of the system. The leads, 2108 and 2109, may include a copper wire body having an optional polymer coat, and may optionally have a distal section made from a different material, such as shape memory materials NiTi, spring steel, or stainless. A shape memory material at the distal end of the lead provides for shape-setting the end portion in order to specify the angle and shape of the lead, thus allowing the lead to make conductive contact with the correct, selected location inside the atrium and ventricle.

Figure 33:
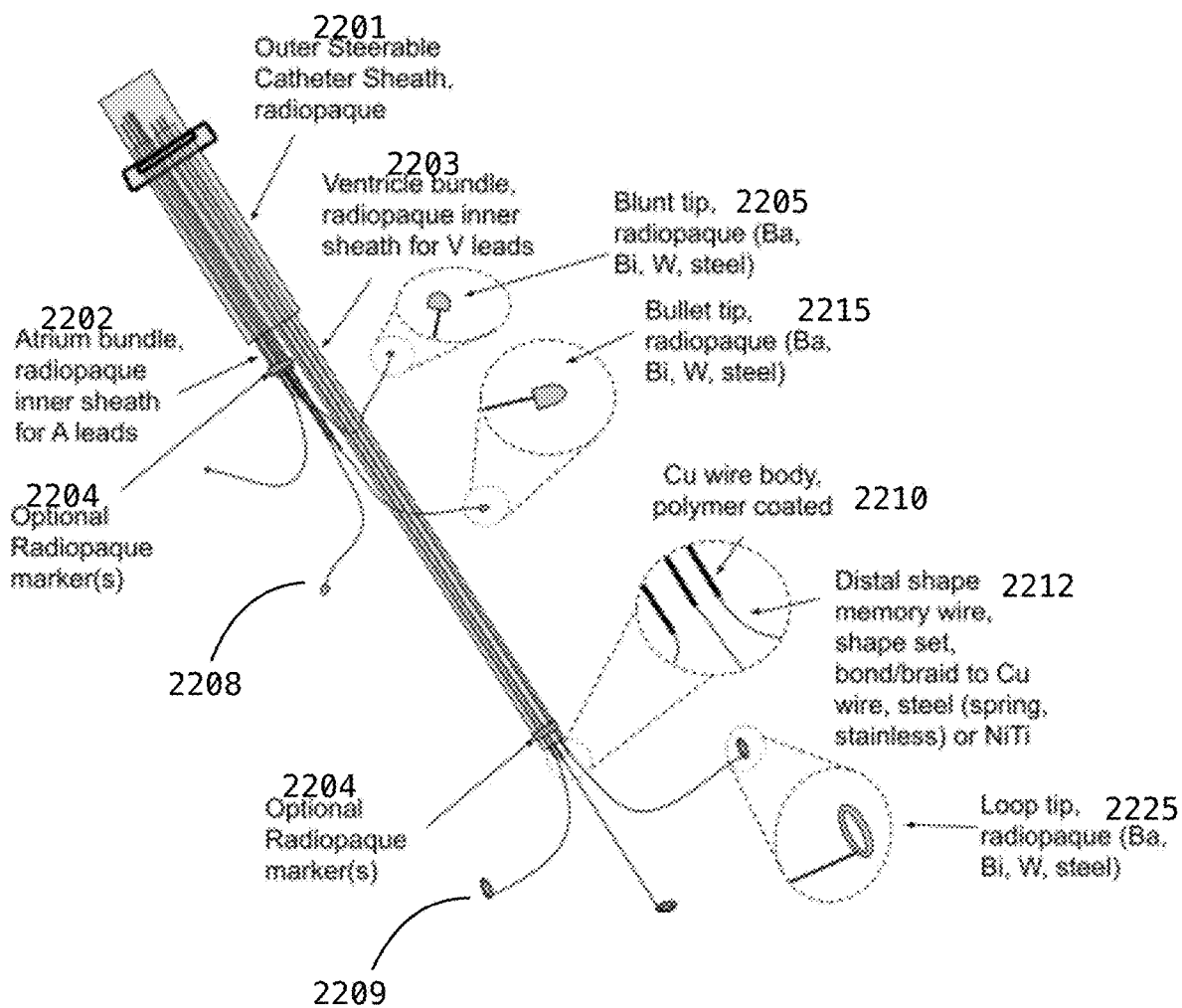
FIG. 33 is an illustration of leads having a shape and constructed of materials to reduce endothelial injury and maximize energy transfer and signal transduction.

FIG. 33 is an illustration of leads having a shape and constructed of materials to reduce endothelial injury and maximize energy transfer and signal transduction. This figure shows the atrium leads and the ventricle leads having different selected electrode tips 2205, 2215, and 2225. The blunt, non-damaging tip 2205 may include radio-opaque materials or coatings. Non-limiting materials may be selected from barium, bismuth, tungsten, steel, or other known RO materials. The bullet-shaped, non-damaging tip 2215 may also include radio-opaque materials or coatings. Non-limiting materials may be selected from barium, bismuth, tungsten, steel, or other known RO materials. The loop-shaped, non-damaging tip 2225 in FIGS. 14-15 may include radio-opaque materials or coatings. Non-limiting materials may be selected from barium, bismuth, tungsten, steel, or other known RO materials. A loop-shaped tip may be indicated when contacting extensively convoluted trabeculae carneae to provide a larger lead surface without perforating or damaging the heart tissue. FIG. 32 also shows outer sheath 2201 having the atrium inner sheath 2202 and the ventricle inner sheath 2203 disposed therein. Atrium leads 2208 and ventricle leads 2209 are shown extending from their respective inner sheaths. Optional radio-opaque markers 2204 may also be mounted at various locations to assist the endoscopic practitioner with visualizing the proper placement of the system. The leads, 2208 and 2209, may include a copper wire body having an optional polymer coat 2010, and may optionally have a distal section 2212 made from a different material, such as shape memory materials NiTi, spring steel, or stainless. A shape memory material at the distal end of the lead provides for shape-setting the end portion in order to specify the angle and shape of the lead, thus allowing the lead to make conductive contact with the correct, selected location inside the atrium and ventricle.

Figure 34:
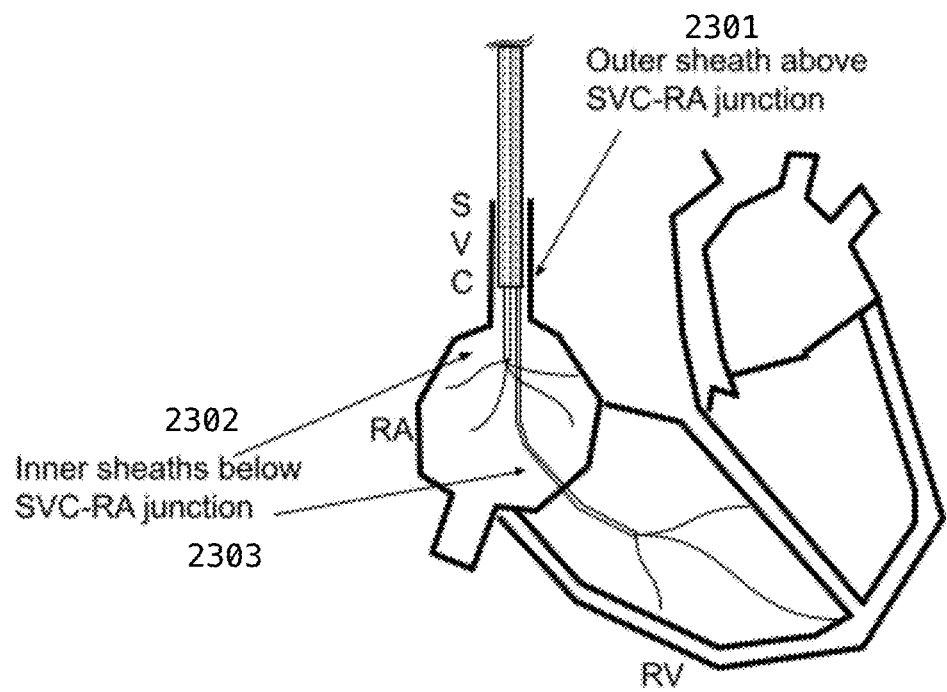
FIG. 34 is an illustration of the outer sheath delivered to a location just above the junction of the superior vena cava and the right atrium ("the SVC-RA junction"), with the inner sheaths delivering their leads to the right atrium and the right ventricle, respectively.

FIG. 34 is an illustration of the outer sheath 2301 delivered to a location just above the junction of the superior vena cava and the right atrium ("the SVC-RA junction"), with the inner sheaths 2302, 2303 delivering their leads to the right atrium and the right ventricle, respectively. This figure shows that the outer sheath may remain within the superior vena cava (SVC), above the junction with the right atrium ("the SVC-RA junction"), while the inner sheaths deliver their leads to their respective chambers, the right atrium (RA) and the right ventricle (RV). During deployment and during withdrawal, providing sequential delivery (and withdrawal) of the outer sheath, then the inner sheaths, and finally the leads, avoids tangling the leads and provides for the correct positioning of each lead to its pre-selected location. This segmentation allows an operator of the system to make an initial deployment of the leads, take impedance or other readings, and then re-position the leads to calibrate, or tune, the energy transfer and/or signal transmission. Re-positioning the leads is provided by the ability to withdraw and re-deploy the system in a segmented manner.

FIG. 35 is a flowchart showing a non-limiting preferred embodiment of the sequential process for deploying and calibrating the leads. This figure shows Step 1: Deploy the transvenous intracardiac pacing catheter to the right ventricle of a patient. Step 2: Partially withdraw the outer sheath to a first position to expose the inner ventricular sheath. Step 3: Partially withdraw the inner ventricular sheath to deploy the shape-set ventricular pacing leads. Step 4: Calibrate the ventricle leads and withdraw and re-deploy the ventricle leads from the inner ventricular sheath as needed. Step 5: Partially withdraw the outer sheath to a second position to expose the inner atrial sheath. Step 6: Partially withdraw the inner atrial sheath to deploy the shape-set atrial pacing leads. Step 7: Calibrate the atrial leads and withdraw and re-deploy the atrial leads from the inner atrial sheath as needed.

It is also within the scope of the invention to sequence the deployment wherein the outer sheath is not delivered all the way into the right ventricle, but is instead Step 1: delivered only to the SVC. In this embodiment, Step 2: the inner ventricle sheath is then extended and deployed to the right ventricle. Then, after the inner ventricle sheath delivers the ventricle leads to the right ventricle, Step 3: the inner ventricle sheath may be withdrawn to expose and deploy the ventricle leads to their functional locations within the right ventricle. In this embodiment, the sequence then has Step 4: the inner atrium sheath being extended and deployed to the right atrium. After the inner atrium sheath delivers the atrium leads to the right atrium, Step 5: the inner atrium sheath may be withdrawn to expose and deploy the atrium leads to their functional locations within the right atrium. As before, optional Step 3b and Step 5b, has the operator calibrating the ventricular leads and atrial leads, and optionally, withdrawing and re-deploying the leads if the impedance or transmission is not in the desired range.

LEGAL EQUIVALENTS

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations.

The embodiments described herein can include various combinations and/or sub-combinations of the functions, components, and/or features of the different embodiments described. Various of the above-disclosed and other features and functions, or alternatives thereof, may be combined into many other different systems or applications. Various presently unforeseen or unanticipated alternatives, modifications, variations, or improvements therein may be subsequently made by those skilled in the art, each of which is also intended to be encompassed by the disclosed embodiments.

The invention claimed is:

1. An electrode system connectable to a pacemaker for sequentially pacing both the atrium and ventricle of a human heart comprising:
a plurality of insulated electrical leads comprising a first set of ventricle leads and a second set of atrium leads, each said lead having an insulated wire and an atraumatic tip, said atraumatic tip comprising a domed head connected to a cylindrical sidewall, said cylindrical sidewall having a sloped proximal edge connected to a tapered coupling, said tapered coupling forming a smooth transition to an outer diameter of the insulated wire,
a ventricular sheath disposed over said first set of ventricle leads, the ventricular sheath being retractable from the ventricle leads to deploy the ventricle leads in the ventricle, each of the ventricle leads having a resiliency and shape to be deployed in contact with the ventricle wall when the ventricular sheath is retracted therefrom,
an atrial sheath disposed over said second set of atrium leads and the ventricular sheath disposed within the atrial sheath along a central axis, the atrial sheath being retractable from the atrium leads to deploy the atrium leads in the atrium, each of the atrium leads having the resiliency and shape to be deployed in contact with the atrium wall when the atrial sheath is retracted,
wherein the ventricle leads are not attachable to the ventricle wall, but are adapted to contact the ventricle wall, and the atrium leads are not attachable to the atrium wall, but are adapted to contact the atrium wall.

2. The electrode system according to claim 1, wherein the first set comprises three ventricle leads and the second set comprises four atrium leads.

3. The electrode system according to claim 1, wherein the electrode system is configured for withdrawal from the heart so that the atrium leads are returnable to the atrial sheath and the ventricle leads are returnable to the ventricular sheath at a location above the SVC-RA junction.

4. The electrode system according to claim 1, wherein the atraumatic tip includes a metal portion comprised of stainless steel, nickel-titanium alloy, gold, platinum, or iridium.

5. The electrode system according to claim 1, wherein the atrium leads are the same length or different staggered lengths, having a pre-set curved shape, and extend about 2.00 inches from a central axis of the atrial sheath.

6. The electrode system according to claim 1, wherein the ventricle leads comprise a straight distal ventricle lead and two pre-set curved shape ventricle leads, the ventricle leads are the same length or different staggered lengths, the straight distal ventricle lead extending along a central axis of the atrial sheath, and the two pre-set curved shape ventricle leads extend about 1.50 inches from the central axis of the atrial sheath.

7. The electrode system according to claim 1, wherein the atrium leads having a length of about 3.14 inches (½C=pi/2*D), having a pre-set curved shape, and extend about 2.00 inches from a central axis of the atrial sheath.

8. The electrode system according to claim 1, wherein the ventricle leads comprise a distal ventricle lead and two pre-set curved shape ventricle leads, the distal ventricle lead having a length of about 2.76+/−0.20 inches extending along a central axis of the atrial sheath, and the two pre-set curved shape ventricle leads having a length of about 2.355 inches (½C=pi/2*D) extend about 1.50 inches from the central axis of the atrial sheath.

9. The electrode system according to claim 1, wherein when deployed in the ventricle, one of said ventricle leads is a distal ventricle lead extending along a central axis of the atrial sheath, and two ventricle leads are memory shape-set at 90 degrees to the central axis and are offset 180 degrees from each other in a plane perpendicular to the distal ventricle lead.

10. The electrode system according to claim 1, wherein when the atrium leads are deployed in the atrium, the atrium leads are memory shape-set at 90 degrees to a central axis of the atrial sheath and offset 90 degrees from each other in a plane perpendicular to the central axis.

11. The electrode system according to claim 1, where the atrium leads and the ventricular leads have different lengths.

12. The electrode system according to claim 1, having a steerable delivery catheter with a female Luer connector, a side-port Tuohy Borst access connector, a deployment stopper, a terminal connection connected to the electrical leads, and an extension hub, the atrial sheath disposed within the steerable delivery catheter, the ventricular sheath disposed within the atrial sheath.

13. The electrode system according to claim 12, wherein the steerable delivery catheter has an inner polymer liner selected from parylene or PTFE, a Tie layer, a braid, an outer jacket, and a heat shrink fusing sleeve located near a distal tip.

14. The electrode system according to claim 12, wherein the steerable delivery catheter has an outer diameter (OD) of 0.104+−0.003 inches, an inner diameter (ID) of 0.090+−0.002 inches, and a working length of 12.00+−0.30 inches.

15. The electrode system according to claim 12, wherein the female Luer connector has a connector orientation that is keyed to a leads orientation of the electrical leads, wherein the connector orientation informs an operator of the leads orientation.

16. The electrode system according to claim 12, wherein the steerable delivery catheter has a dead-stop marker to indicate a maximum safe distance of insertion of the electrical leads.

17. The electrode system according to claim 1, wherein the ventricular sheath comprises a stoplight extrusion having three (3) conduits (lumens), the inner diameter of the three conduits (lumens) configured to deliver the ventricular leads.

18. The electrode system according to claim 1, wherein the atrial sheath comprises a 4-in-1 extrusion having a central axial conduit (lumen) and four perimeter conduits (lumens), the inner diameter of the central axial conduit (lumen) configured to deliver the ventricular sheath, and the inner diameter of the four perimeter conduits (lumens) configured to deliver the atrial leads.

19. The electrode system according to claim 1, wherein the atrial sheath and the ventricular sheath have radioopaque distance markers.

20. The electrode system according to claim 1, wherein the electrical leads are monopolar, either positive or negative polarity.

21. The electrode system according to claim 1, wherein when connected to a pacemaker, the distal ventricle lead and a second ventricle lead have a signal of a first polarity, and a third ventricle lead has a signal of an opposite polarity.

22. The electrode system according to claim 1, wherein when connected to a pacemaker, two of the atrium leads have a signal of a first polarity and two of the atrium leads have a signal of an opposite polarity.

23. The electrode system according to claim 1, wherein the insulated wire of each of the atrium leads and the ventricle leads are radio-opaque, comprised of parylene, PTFE or PTE, and prevent cross-talk.

24. The electrode system of claim 1, wherein the atraumatic tip of the atrium leads and the ventricle leads are the same size or different.

25. The electrode system of claim 1, wherein the atrium leads each have an atraumatic tip with an outer diameter of 8 Fr (8×0.33 mm=2.64 mm=0.1039 in).

26. The electrode system of claim 1, wherein at least two of the ventricle leads each have an atraumatic tip with an outer diameter of 8 Fr (8×0.33 mm=2.64 mm=0.1039 in).

27. The electrode system of claim 1, wherein one of the ventricle leads is a distal ventricle lead and has an atraumatic tip with an outer diameter of 11 Fr (11×0.33 mm=3.63 mm=0.1429 in).

28. The electrode system of claim 1, wherein the insulated wire having a fibrin-resistant coat along at least a part thereof, the fibrin-resistant coat comprised of parylene, silicone, siloxane, PEEK, PET, PFTE, or parylene co-polymer doped with a releasable anti-coagulant drug or anti-inflammatory drug.

29. The electrode system according to claim 1, wherein each of said electrical leads has a proximal portion made from wire with a radio-opaque material and a distal portion made from a shape memory material.

30. The electrode system according to claim 1, wherein each of said atraumatic tips has a radio-opaque material.

31. The electrode system according to claim 1, wherein
the ventricular sheath and atrial sheath are each made from a polymer that is doped in at least one segment with a radiopaque material to form a radiopaque polymer sheath,
each of the ventricle and atrium leads have a proximal body portion, a distal end portion, and the atraumatic tip,
the proximal body portion made from a radiopaque polymer-covered copper wire,
the distal end portion made from shape memory material, the shape memory material selected from stainless steel, spring steel, cobalt-chromium alloy, nickel-titanium alloy, and mixtures thereof,
the atraumatic tip made from a pulse transmitting material and a radiopaque material, the radiopaque material selected from a barium-containing compound, a bismuth-containing compound, a steel compound, a tungsten-containing compound, and mixtures thereof, two of the three ventricle leads are memory shape-set at a 90 degree angle in an expanded configuration, and the two ventricle leads are offset 180 degrees from each other, one of the three ventricle leads is a distal ventricle lead extending along a central axis of the atrial sheath, each of the four atrium leads are memory shape-set at a 90 degree angle in an expanded configuration, and each of the four atrium leads are separated 90 degrees from each other, the atrial sheath and the ventricle sheath are each comprised of a distal portion and a proximal portion, and each has a distance marker every 10 cm along its entire length.

32. The electrode system according to claim 1, wherein the atrium leads and the ventricle leads each connect to lead terminals that extend from a cable junction housing to a pacemaker, wherein the pacemaker comprises computer program instructions readable by a processor to provides functions selected from the group consisting of: a diagnostic function, a sensor operation, a stimulation signal, a program for an individual lead for sensing, a program to reduce over-sensing of the ventricular leads by T-waves or other noise or attenuating or interfering signals, a program to reduce over-sensing of the atrium leads by the R-wave, a program to minimize cross-talk, and a program to adjust sensing and stimulation on a lead-by-lead basis.

33. The electrode system according to claim 1, wherein the atrium leads are memory shape-set to sense and stimulate an atrial endothelium area of the heart, the ventricle leads are memory shape set to sense and stimulate a ventricular endothelium area of the heart.

34. The electrode system according to claim 1, wherein each of said ventricle leads is connected to a ventricular sensor or stimulator in a pacemaker and each of said atrium leads is connected to an atrium sensor or stimulator in said pacemaker.

35. The electrode system according to claim 1, wherein the electrical leads are connected to a pacemaker that includes two sequential pulse generators to provide sensing and stimuli for a ventricle and for an atrium for sequentially pacing both the atrium and ventricle of a heart in the "dual chamber" mode.

36. The electrode system according to claim 35, wherein the pacemaker includes computer program instructions executable by a processor for performing digital signal processing for the ventricle leads and the atrium leads, wherein the digital signal processing is selected from the group consisting of: multiple input, multiple output (MIMO), single input multiple output (SIMO), single input single output (SISO), and multiple input single output (MISO).

37. The electrode system according to claim 36, wherein the computer program instructions executable by a processor provides one or more functions selected from:
decreasing sensitivity of certain leads and increasing sensitivity of other leads during a depolarization cycle (PQRST) allows the invention to increase SNR in the sensing function, decreasing or increasing stimulatory signals to one or more leads allows the invention to more accurately provide stimulation to the atrial endothelium, ventricular endothelium, or other cardiac tissue to provide a level of granularity to the stimulation function, programming leads so that sensing leads are not required to share the function of a shocking/stimulation leads, and bypassing damaged or degraded leads to allow continued functioning without requiring the entire device to be removed from a patient, this increasing the longevity of implanted devices using the inventive technology.

38. A method for quickly deploying a cardiac pacing device to a heart in a patient, comprising:
(i) Providing the system in 1;
(ii) Accessing a jugular vein in the patient and advancing the catheter sheath under ultrasound or other non-fluoroscopic imaging modality to a right ventricle of the heart of the patient;
Withdrawing the outer catheter sheath to a first position to deploy the first set of three ventricle leads;
(iv) Withdrawing the outer catheter sheath to a second position to deploy the second set of four atrium leads;
(v) Performing a diagnostic test using the first set of three ventricle leads and the second set of four atrium leads to identify patient cardiac patterns and to validate the operation of the system;

(vi) Performing a cardiac pacing routine appropriate as a treatment for the patient cardiac pattern using the system.

39. The method according to claim 38, wherein performing steps (i)-(iv) are performed in a time period no longer than 3-5 minutes.

40. The method according to claim 38, wherein the system is deployed in a patient for a time period from 1 hour up to 7 days of use.

* * * * *